United States Patent [19]

Liu et al.

[11] Patent Number: 5,667,652
[45] Date of Patent: Sep. 16, 1997

[54] MULTI-FUNCTIONAL SENSOR FOR COMBUSTION SYSTEMS

[75] Inventors: Meilin Liu, Gwinnett County, Ga.; Liang Jun Li, Salt Lake City, Utah

[73] Assignee: Gas Research Institute, Chicago, Ill.

[21] Appl. No.: 482,958

[22] Filed: Jun. 15, 1995

Related U.S. Application Data

[63] Continuation of Ser. No. 164,143, Dec. 9, 1993, abandoned.

[30] Foreign Application Priority Data

Nov. 19, 1993 [WO] WIPO .................. PCT/US93/11274

[51] Int. Cl.⁶ .................. G01N 27/407; G01N 27/409
[52] U.S. Cl. .................. 204/412; 204/421; 204/424; 204/425; 204/426; 204/427; 205/775; 205/784
[58] Field of Search .................. 204/412, 421–429; 205/775, 783.5, 784, 784.5

[56] References Cited

U.S. PATENT DOCUMENTS

| | | | |
|---|---|---|---|
| 3,989,614 | 11/1976 | Tien | 204/426 |
| 4,044,601 | 8/1977 | Sakurai et al. | 73/23 |
| 4,135,381 | 1/1979 | Sherwin | 73/23 |
| 4,151,503 | 4/1979 | Cermak et al. | 338/14 |
| 4,190,499 | 2/1980 | Pebler | 204/153.1 |
| 4,227,974 | 10/1980 | Petersen et al. | 204/1 |
| 4,272,331 | 6/1981 | Hetrick | 204/1 T |
| 4,292,158 | 9/1981 | Muller et al. | 204/429 |
| 4,298,573 | 11/1981 | Fujishiro | 204/426 |
| 4,300,991 | 11/1981 | Chiba et al. | 204/195 |
| 4,305,724 | 12/1981 | Micko | 23/232 E |
| 4,306,957 | 12/1981 | Ishitani et al. | 204/426 |
| 4,314,996 | 2/1982 | Sekido et al. | 422/98 |
| 4,345,985 | 8/1982 | Tohda et al. | 204/192 |
| 4,356,065 | 10/1982 | Dietz | 204/1 |
| 4,487,680 | 12/1984 | Logothetis et al. | 204/426 |
| 4,502,939 | 3/1985 | Holfelder et al. | 204/429 |
| 4,522,690 | 6/1985 | Venkatasetty | 204/412 |
| 4,570,479 | 2/1986 | Sakurai et al. | 204/426 |
| 4,572,900 | 2/1986 | Wohltjen | 436/151 |
| 4,792,433 | 12/1988 | Katsura et al. | 422/98 |
| 4,832,818 | 5/1989 | Sekido et al. | 204/412 |
| 4,990,235 | 2/1991 | Chujo | 204/424 |
| 5,012,671 | 5/1991 | Yagawara et al. | 73/31.06 |
| 5,120,422 | 6/1992 | Liu et al. | 204/416 |
| 5,173,166 | 12/1992 | Tomantschger et al. | 204/426 |
| 5,178,744 | 1/1993 | Nakazawa et al. | 204/425 |
| 5,226,309 | 7/1993 | Stetter et al. | 73/31 |
| 5,273,628 | 12/1993 | Liu et al. | 204/296 |
| 5,279,145 | 1/1994 | Suzuki | 73/23.32 |
| 5,397,442 | 3/1995 | Wachsman | 204/153.16 |

FOREIGN PATENT DOCUMENTS

| | | | |
|---|---|---|---|
| 0025625 | 3/1981 | European Pat. Off. | G01N 27/56 |
| 3525774 | 1/1987 | Germany | G01N 1/28 |
| 5599063 | 7/1980 | Japan . | |
| 0084552 | 4/1986 | Japan | G01N 27/58 |
| 1076948 | 4/1986 | Japan . | |
| 225741 | 1/1990 | Japan . | |
| 404348268 | 12/1992 | Japan | G01N 27/12 |

OTHER PUBLICATIONS

Liaw et al, "Low Temperature Limiting-Current Oxygen Sensors Based on Tetragonal Zirconia Polycrystals", J. Electrochem. Soc. vol. 138, No. 8, Aug. 1991, pp. 2478–2483.

Liu, M., et al., *Amperometric Sensors Based on Ceramic Membranes*, 19 May, 1993.

(List continued on next page.)

*Primary Examiner*—T. Tung
*Attorney, Agent, or Firm*—Dick and Harris

[57] ABSTRACT

Disclosed is a multi-functional voltammetric or amperometric sensor useful for sensing components of the exhaust stream of a combustion system. The disclosed sensor (110) includes a solid oxide ion-conductive electrolyte membrane (112) having two sides (114, 116). On one side is a working electrode (120), preferably covered by a diffusion barrier (126) exposed to the exhaust stream. On the other side (116), preferably exposed to air, is a counter-electrode (122) and, optionally, an reference electrode (124). Meters are provided to measure a current flex between the working and counter-electrodes.

15 Claims, 26 Drawing Sheets

OTHER PUBLICATIONS

Liu, M., *Electrode Kinetics and Transport Properties of Mixed Ionic–Electronic Conductors,* Ionic and Mixed Conducting Ceramics, PV–91–12, pp. 191–215, 1991; month unavailable.

Liu, M., *Theoretical Assessment of Oxygen Separation Rates of Mixed Conductors,* Ionic and Mixed Conducting Ceramics, PV–91–12, pp. 95–109, 1991; month unavailable.

Logothetis, E.M., et al., *A High–Sensitivity Sensor for the Measurement of Combustible Gas Mixtures,* Sensors and Conductors, 9, pp. 363–372, 1986; month unavailable.

Liu, M., *Oxygen Sensors,* ASM Engineered materials Handbook, vol. 4, Ceramics and Glasses, pp. 363–372, 1986; month unavailable.

Heyne, L., *Some Properties and Applications of Zirconia–Based Solid–Electrolyte Cells,* Eindhoven, pp. 65–88, Sep. 1974.

Usiu, T. et al., *Gas Polarographic Oxygen Sensor Using an Oxygen/Zirconia Electrolyte,* J. Electrochem., Soc., vol. 135, No. 2, pp. 534–542, Feb., 1989.

Logothetis, E.M., $ZrO_2$ *Oxygen Sensors in Automotive Applications,* Advances in Ceramics, vol. 3, Science and Technology of Zirconia (The American Ceramic Society 1981); month unavailable.

Liu et al., *Characterization of Mixed Ionic–Electronic Conductors,* published before Apr. 6, 1994.

Heyne et al., "The Speed of Response of Solid Electrolyte Galvanic Cells for Gas Sensing", Journal of the Electrochemical Society, vol. 124, pp. 727–735, May, 1977.

Liu et al., "Multifunctional Sensors Based on Ceramic Electrolytes", May 19, 1993.

Ogata et al., "$CO_2$ gas sensor using $\beta$–$Al_2O_3$ and metal carbonate", Journal of Materials Science Letters, 5, pp. 285–286, 1986 month unavailable.

Sandler, Y.L., "The Response of the Stabilized Zirconia Galvanic Cell to Methane–Oxygen Mixtures", Journal of the Electrochemical Society, vol. 118, No. 8, pp. 1378–1381, Aug., 1971.

Fukui et al., "CO Detection by BaO and $Y_2O_3$ Dispersed $SnO_2$ Ceramics", Symp. Proc. on Chemical Sensors, Electrochem. Soc., ed. D.R. Turner, pp. 187–195, 1987 month unavailable.

Liaw et al., "Novel Hydrogen Sensors For Use At Elevated Temperatures", Symp. Proc. on Chemical Sensors, Electrochem. Soc., ed. D.R. Turner, pp. 91–98, 1987 month unavailable.

Uchida et al., "High Temperature Hydrogen Sensor And Steam Sensor Using $BaCeO_3$–Based Proton Conducting Ceramics", Symp. Proc. on Chemical Sensors, Electrochem. Soc., ed. D.R. Turner, pp. 172–179, 1987 month unavailable.

Usui et al., "Solid State Humidity Sensor Usable At High Temperatures", Symp. Proc. on Chemical Sensors, Electrochem. Soc., ed. D.R. Turner, pp. 202–211, 1987 month unavailable.

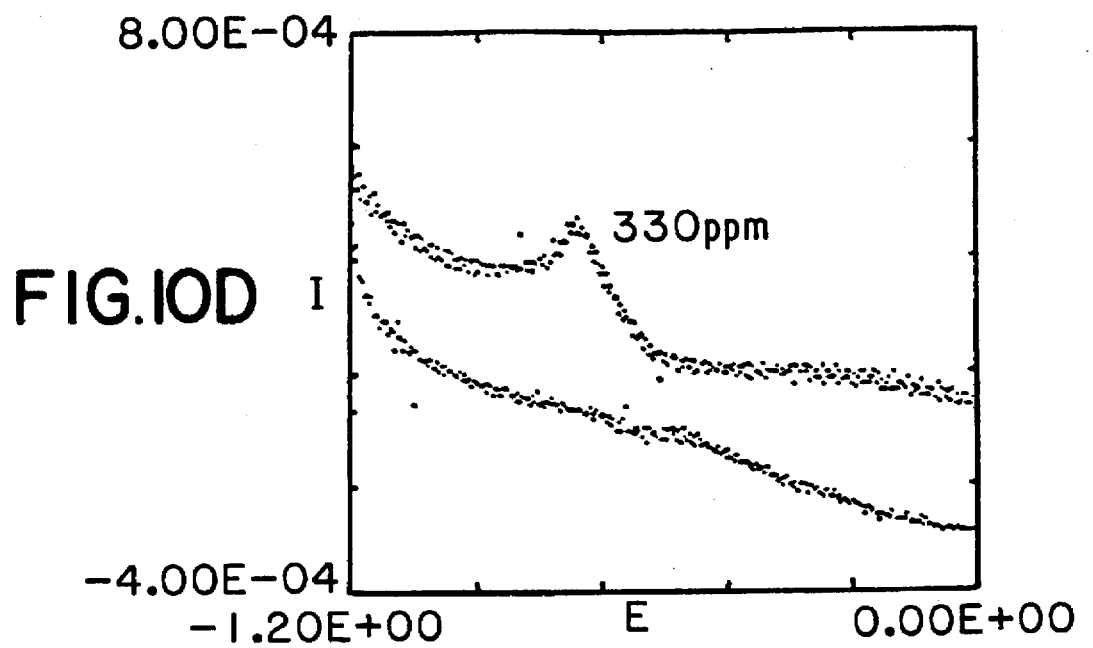
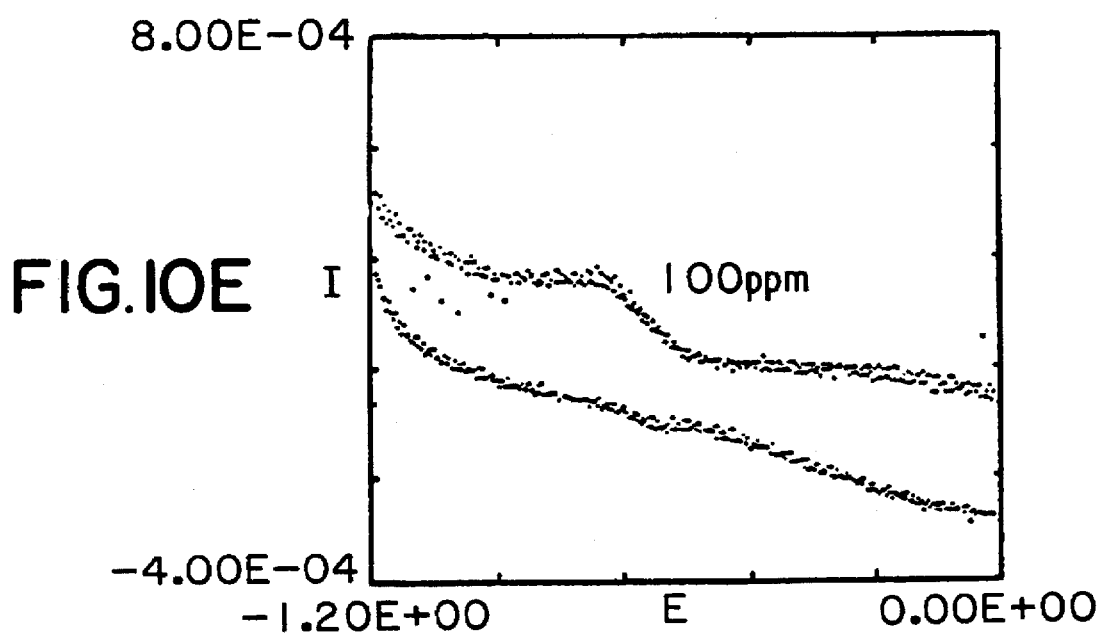

500°C

400°C

450°C

350°C

500ppm NO + H$_2$

500ppm NO + 500ppm CH$_4$

500ppm NO +10% CO$_2$

500ppm NO + 500ppm CO

500ppm NO + 500ppm H$_2$

500ppm NO + 500ppm H$_2$ + 0.7% O$_2$

500ppm NO (dry)

500ppm NO + 25% H$_2$O

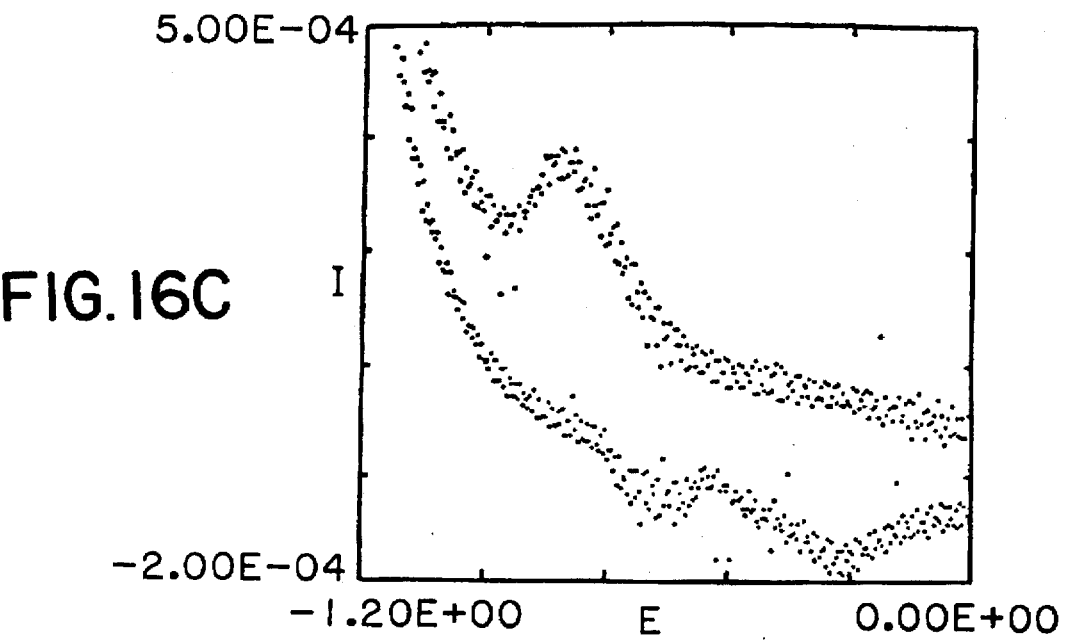
500ppm NO + 3% H$_2$O
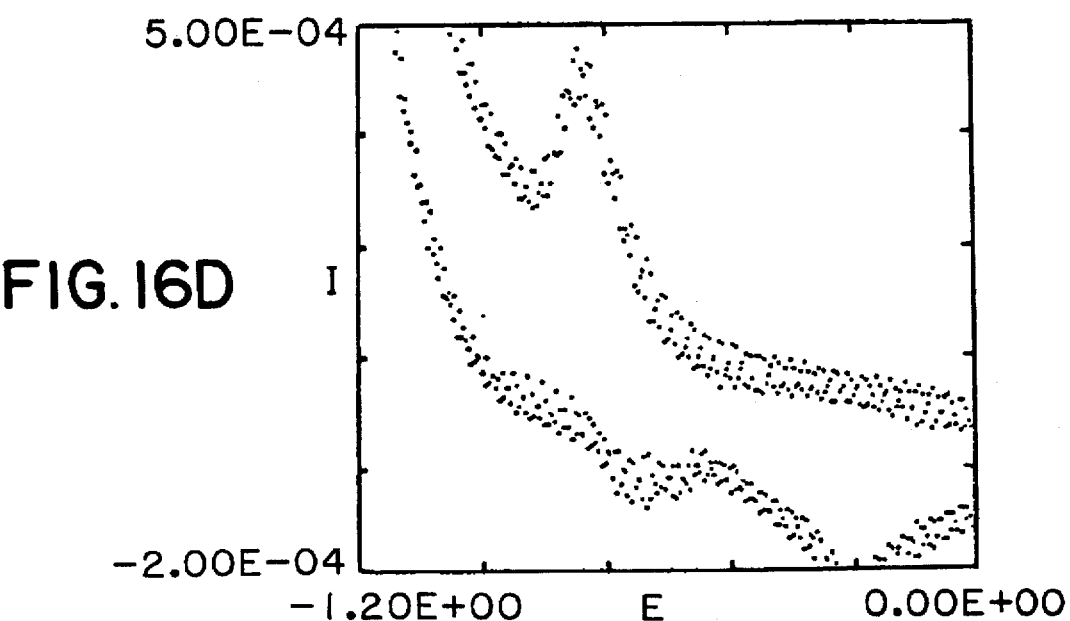
500ppm NO (dry), AFTER SENSOR TESTED IN MOISTURE ENVIRONMENT.

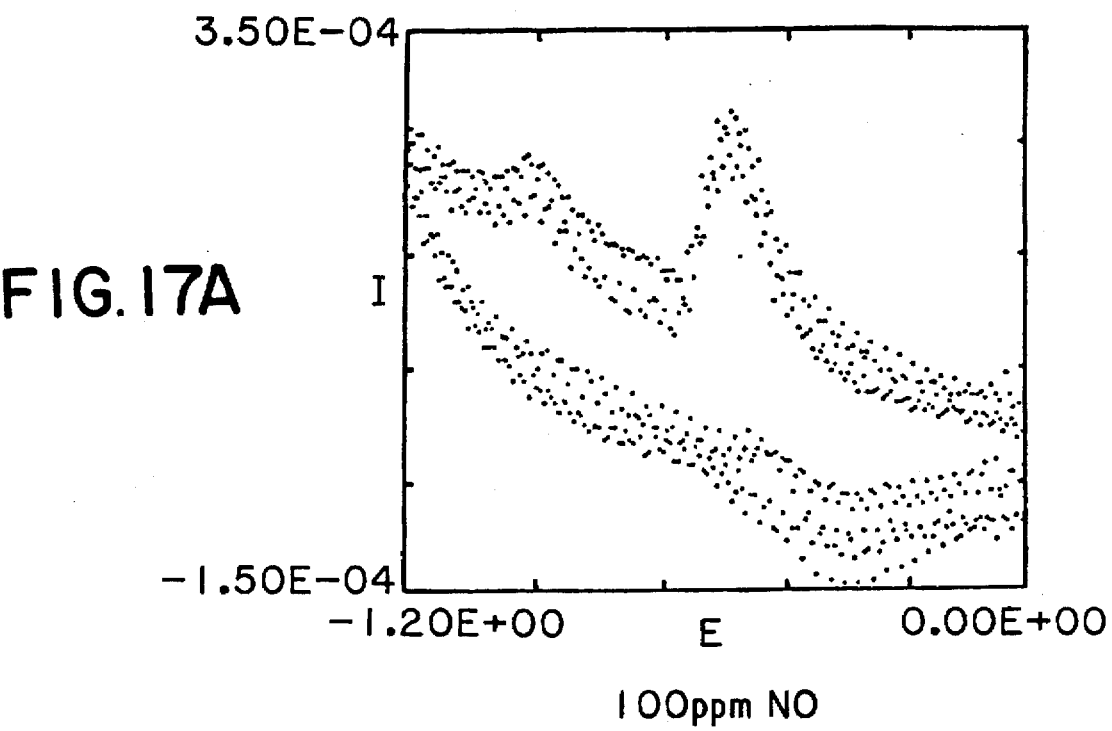
100ppm NO
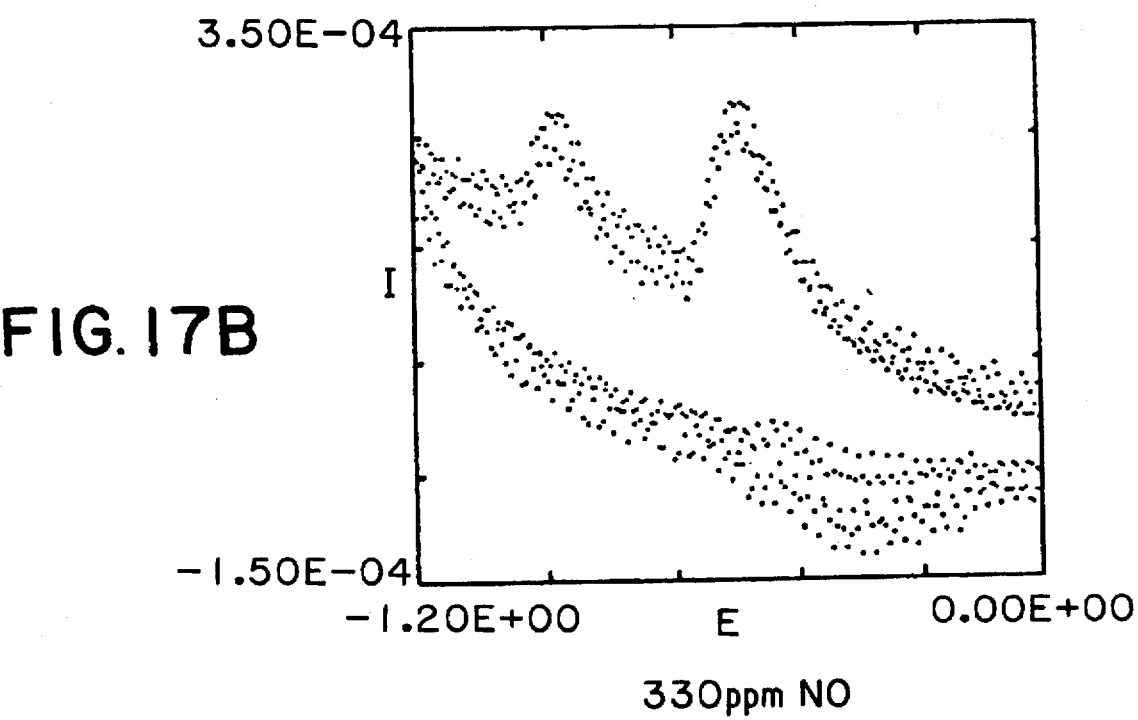
330ppm NO

200ppm NO

500ppm NO

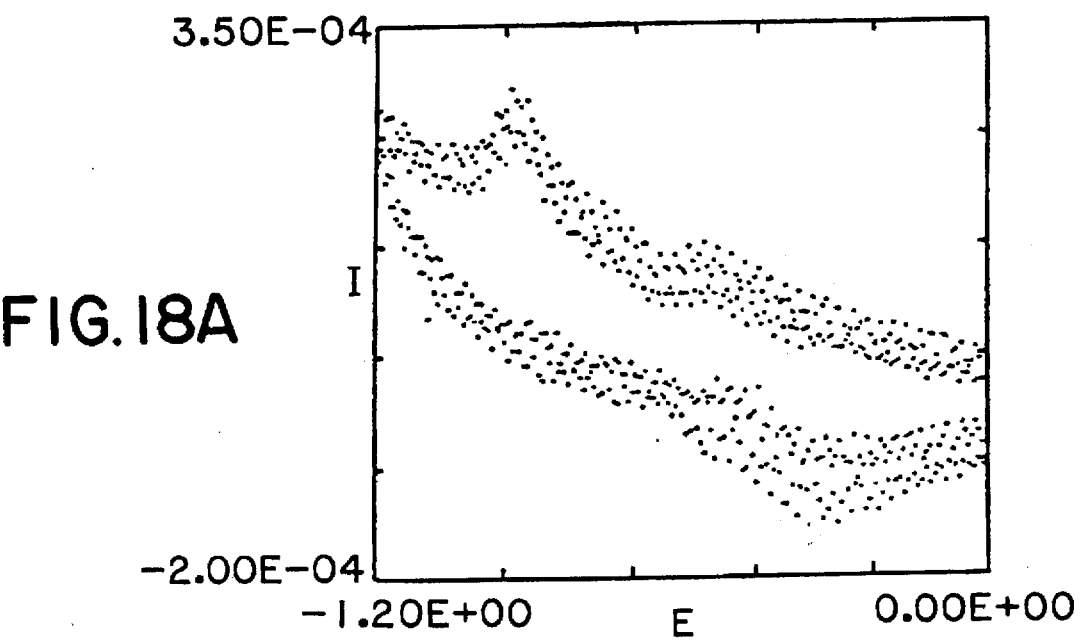
0.2% O₂
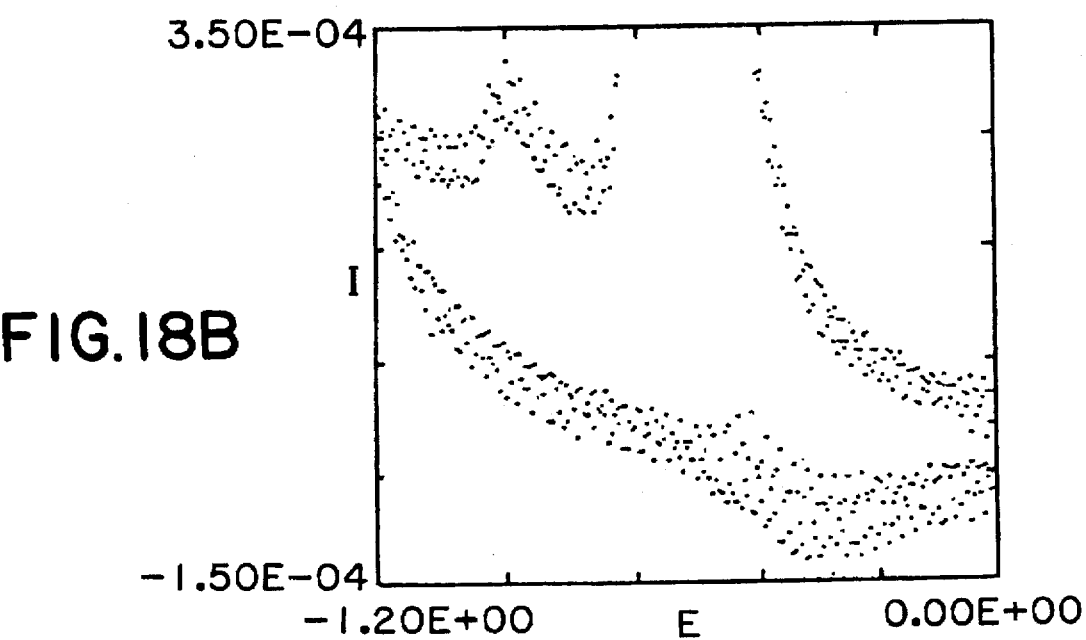
2.1% O₂

0.67% $O_2$ 4.2% $O_2$

1000ppm NO

800ppm NO + 0.4% $O_2$

1000ppm NO

800ppm NO + 0.4% O₂

MULTI-FUNCTIONAL SENSOR FOR COMBUSTION SYSTEMS

This is a continuation of application Ser. No. 08/164,143, filed Dec. 9, 1993, now abandoned.

TECHNICAL FIELD

The invention relates generally to sensors for sensing gaseous components in the exhaust stream of combustion systems, and more particularly to multi-functional sensors for combustion control systems for selective and simultaneous sensing of more than one gaseous component in the exhaust stream from a combustion system.

BACKGROUND

Combustion systems convert potential chemical energy in fuels (e.g. natural gas, hydrocarbon, or hydrogen) into another form of energy such as heat or kinetic energy. The fuel is mixed with air or oxygen and combusted, whereupon the combustion products and unburned fuel and air are exhausted from the system in a gaseous stream. Well-known combustion systems include a wide variety of devices including boilers, furnaces, and reciprocating engines.

Both the efficiency and performance of a combustion system can be improved by regulation of the combustion process. For example, precise control of the fuel to air ratio can significantly reduce fuel consumption, while simultaneously reducing toxic emissions in the exhaust stream. Regulation is typically accomplished by a control system that monitors the concentration of combustion products such as nitrogen oxides ($NO_x$), carbon monoxide (CO), and unburned fuel and air in the exhaust stream. The relative concentrations of these exhaust components provides information regarding the combustion system's operation. Important operating parameters such as the fuel to air ratio may then be adjusted to improve operation of the combustion system. Although the requirements of control systems are specific for each different combustion process, the principles governing the control mechanism are similar.

Several problems exist with regard to current sensing technology used in combustion control systems. Most existing sensors are capable of monitoring only a single exhaust gas component at a time in a combustion process. This component, typically $O_2$, is continuously monitored and the concentrations of other components are estimated based on mass balance and thermodynamic equilibrium. However, combustion is a highly non-equilibrium process, so concentrations determined in this manner may be inaccurate. Potentiometric sensing of other combustion product gases such as $NO_x$, $SO_x$, $CO_x$, and $H_2S$, and unspent fuel gases such as $CH_4$ and $C_3H_8$, have been reported but the sensors have demonstrated limited performance. Control systems could be significantly improved if several gaseous components could be accurately monitored simultaneously.

Several ex-situ techniques based on optical phenomena are capable of multi-functionality, but suffer from other disadvantages. For example, Fourier Transform InfraRed (FTIR), and Non-Dispersive InfraRed (NDIR) sensors can accurately monitor multiple gas concentrations, but are very large and expensive. Further, these sensors require the installation of gas sampling lines which makes the sensors cumbersome, and significantly delays control system response. Other ex-situ techniques such as Gas Chromatography (GC), Mass Spectrometry (MS) and most traditional chemical analysis methods are less expensive but are also cumbersome and time consuming. For these reasons, ex-situ sensors based on FTIR, NDIR, GC and MS, and traditional chemical methods are impractical for combustion control systems.

A need exists for a simple, low-cost, multi-functional sensor capable of sensing more than one gas component simultaneously. The sensor should be reliable and accurate, and be able to withstand the harsh environment of the exhaust stream from an operational combustion system.

DISCLOSE OF THE INVENTION

The invention includes a multi-functional sensor which can simultaneously sense more than one gas component in a combustion system's exhaust stream. The sensor is based on electrochemical principles, which permit simplicity and low-cost in both construction and operation. Further, the sensor uses an ion-conducting solid oxide electrolyte material, which is particularly suitable for use in the harsh temperature environment in the exhaust stream of, for example, a natural gas combustion system. The sensor provides increased flexibility during operation since it is operable in either a voltammetric or amperometric mode.

The sensor includes a solid oxide ion-conductive electrolyte membrane having a first surface proximal the exhaust gases of a combustion system, and a second surface isolated from the exhaust gases. The first surface of the membrane is associated with (e.g. adhered, annealed, etc.) a sensing electrode including finely divided catalyst material capable of catalyzing the electrochemical reduction or oxidation of at least one gaseous component from the exhaust gas stream. The sensing electrode may in turn be coated with a porous diffusion barrier to limit diffusion of certain components in the exhaust stream to the electrode surface. The second surface of the electrolyte membrane is associated with a counter-electrode including finely divided catalyst material suitable for catalyzing electrochemical reduction or oxidation of the chemical species electrochemically reduced or oxidized at the sensing electrode. Optionally, a reference electrode may be associated with the second surface proximal the counter-electrode.

The ion-conductive electrolyte membrane is permeable only to a specific chemical species. For example, in a sensor for use with oxygen-containing gases ($NO_x$, $SO_x$, $CO_x$, $O_2$, etc.), the electrolyte membrane is permeable only to oxygen ions. In a sensor for use with hydrogen containing gases ($CH_4$, $H_2S$, etc.) the electrolyte membrane is permeable only to protons.

It is the electrode material, however, that provides multi-function sensing operation. Different electrode materials, each highly selective for a specific gaseous component, may be integrated onto a single electrolyte membrane. In this manner, sensors highly selective for specific gaseous components may be constructed.

In operation, for example in a sensor for use with oxygen-containing gases, exhaust gases from a natural gas combustion system are allowed to contact the sensing ("working") electrode surface. A negative potential is applied to the sensing electrode to facilitate electrochemical reduction of at least one oxygen-containing gaseous component of the exhaust stream. When a negative potential sufficient to reduce an oxide to be sensed is applied to the sensing electrode (the cathode) with respect to the reference electrode (optionally contained within an enclosed air atmosphere), the oxide is reduced. The oxygen ions are then conducted through the ion-conductive electrolyte membrane to the counter-electrode electrode (the anode) where they oxidize to oxygen molecules. Electrons involved in the reaction flow from the anode to the cathode through an electrical connection (e.g. wire) enabling measurement of an electrical current proportional to the concentration of the chemical species involved. In an exhaust stream, each oxide couple (e.g. $NO_x/N_2$, $CO_2/CO$) has a characteristic reduction potential which occurs over a potential range which depends on the concentrations of reactants and products associated with the redox reaction. It is this characteristic range that enables different redox couples to be readily distinguished from other components in the exhaust gas.

Under the condition that gas diffusion through the diffusion barrier is highly restricted, i.e., the gas mixture near the sensing electrode surface is barely convective, sensor response will show standard steady-state voltammetric waves. Current peaks will occur at discrete characteristic potentials associated with certain oxide pairs. In a multi-component system having multiple sensing electrodes on a single electrolyte membrane, with each electrode highly selective for a specific gaseous component, the diffusion of each species is independent of concentration gradients of other species. The fluxes are therefore additive making peak currents the sum of the individual fluxes of each redox species. In an i-E or i-t curve for a gas mixture the peak currents for redox pairs having higher reduction potentials can be corrected using the decaying current of the previous wave as the baseline.

A given species can be distinguished by the characteristic potential (Ep) at which current reaches a maximum, while the species' concentration can be estimated from the peak current ($i_p$). In general, the peak current can be expressed by the following equation:

$$i_p = (nFA)\left(\frac{nF}{RT}\right)^{1/2} (\nu D_{gas})^{1/2} C_{gas} K(\alpha, \Lambda)$$

wherein n is the number of electrons involved in the redox reaction of a particular of gas molecule, F is Faraday's constant, A is the active surface area of sensing electrode, R is the gas constant, T is the absolute temperature, v is the potential sweep rate, $D_{gas}$ is the diffusion coefficient of gas molecule in the diffusion barrier, and $C_{gas}$ is the gas concentration in the sample mixture. The reversibility of electrode kinetics is taken into consideration by the function $K(\alpha,\Lambda)$ which depends on the sensor's design and operating conditions and affects the interpretation of experimental data. However, for a given sensor and a given gas species at a chosen potential scan rate, the peak current is directly proportional to the concentration by:

$$i_p = B_1 \cdot C_{gas}$$

where constant $B_1$ depends upon the sensor design, the gas species to be detected, and the potential sweep rate, can be easily determined experimentally by calibration.

When gas diffusion through the diffusion barrier is hardly restricted, i.e., the gas mixture near the sensing electrode surface is finely convective, sensor response will show steady-state voltammetric waves under convective conditions. In this case, current plateaus are expected to occur in mass-transfer-limited regions.

For a multi-component system, if the subsequent process does not commence until the current plateau has been reached of the previous process, each component gas can be detected independently and distinguished by the potential at which the limiting current occurs. Each gas component's concentration can be estimated from the limiting current associated with the gas. Again, the limiting current for the subsequent process is corrected by subtracting the limiting current of the previous process. In general, the limiting current (current plateaus) can be expressed as:

$$i_l = \frac{(nFA)D_{gas}C_{gas}}{\delta}$$

where n, F, A, $D_{gas}$, and $C_{gas}$ are as defined above and $\delta$ is the diffusion barrier's thickness. For a given sensor and gas species, the limiting current is directly proportional to the concentration as determined by:

$$i_l = B_2 \cdot C_{gas}$$

where the constant $B_2$ is dependent upon sensor design and the gas species to be detected and can be easily determined experimentally by calibration.

While the configuration of sensors for hydrogen-containing gases is similar to that for oxygen-containing gases, the electrolyte and electrode material differ. Proton conductors are employed as electrolyte membranes, and the sensing electrode (the anode) consists of finely-divided particles of catalyst such as Pt, Ni, etc. (for oxidation of $H_2$ or hydrocarbons) deposited on the electrolyte membrane. The counter-electrode (the cathode) may also consist of Pt or Ni, and may be exposed to air, whereas the reference electrode is exposed to a hydrogen-containing atmosphere. The correlation between the sensor response (either $i_t$ or $i_p$) and the concentration of the species to be sensed is the same as that described with regard to sensing of oxygen-containing gases.

In a multi-function sensor having more than one sensing electrode on an electrolyte membrane, the catalysts used for a particular species absorb the species at the electrode surface, while other gas components in the mixture are barred access to the electrode. Sensor response here relates directly to the surface coverage $\theta$ while one obtains the gas concentration in the exhaust mixture from a suitable adsorption isotherm.

The sensor response is related to the activity $a_t$ of the adsorbed species which is related to the concentration of species t through activity coefficient $Y_t$ and $C_t$ is the species concentration t in the bulk phase.

$$a_t = Y_t \cdot C_t$$

The sensor also operates in an amperometric mode wherein a steady electrical potential is applied to the sensor and the current response carries information about the chemical species undergoing reduction or oxidation. The advantages of amperometric sensors include fast response, high sensitivity to the species being detected, insensitivity to interference species, simplicity in fabrication, high stability and reliability, and low cost. The most attractive feature of amperometric sensors is the fast response (less than 30 seconds) to concentration changes in oxygen. Sensitivity to oxygen, particularly in low concentration range, is also high.

BRIEF DESCRIPTION OF THE DRAWINGS

FIG. 10D is a cyclic voltammogram of a NO sensor in a gas mixture containing 330 ppm NO.

FIG. 10E is a cyclic voltammogram of a NO sensor in a gas mixture containing 100 ppm NO.

FIG. 16C is a cyclic voltammogram of a $NO_x$ sensor in 500 ppm NO with 3% $H_2O$ vapor.

FIG. 16D is a cyclic voltammogram of a $NO_x$ sensor in 500 ppm NO with no $H_2O$ vapor, after the sensor had been tested in a moisture environment.

FIG. 17A is a cyclic voltammogram of a $NO_x$ sensor at 100 ppm NO in a mixture of interfering species of $CO_2$, $CH_2$, $O_2$, and $H_2O$.

FIG. 17B is a cyclic voltammogram of a $NO_x$ sensor at 330 ppm NO with the same mixture of interfering species as in FIG. 17A.

FIG. 18A is a cyclic voltammogram of a $NO_x$ sensor in an environment of NO, $CO_2$, $CH_4$ and $H_2O$, with 0.2% $O_2$.

FIG. 18B is a cyclic voltammogram of the $NO_x$ sensor of FIG. 18A, with the same concentration of NO, $CO_2$, $CH_4$ and $H_2O$, with 2.1% $O_2$.

BEST MODE OF THE INVENTION

Figure 1:
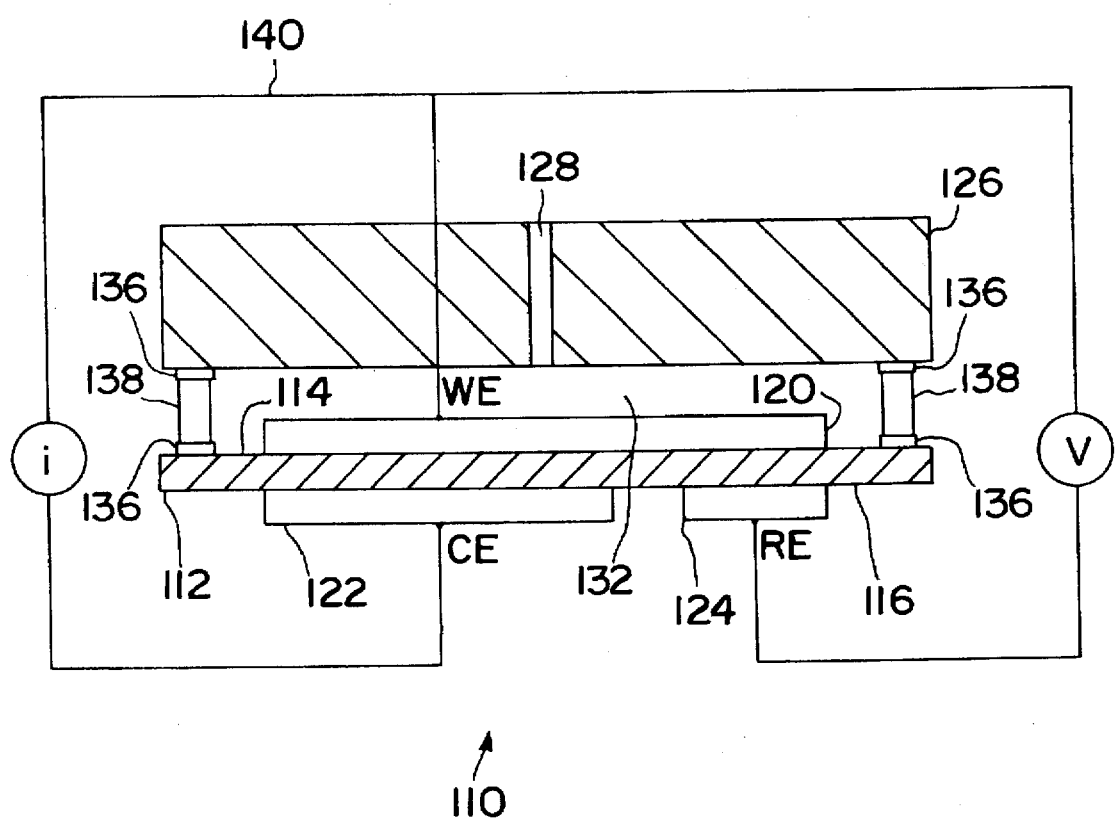
FIG. 1 is a schematic drawing of a multi-function sensor based on voltammetric principles for use in a control system for natural gas combustion systems.
Figure 2:
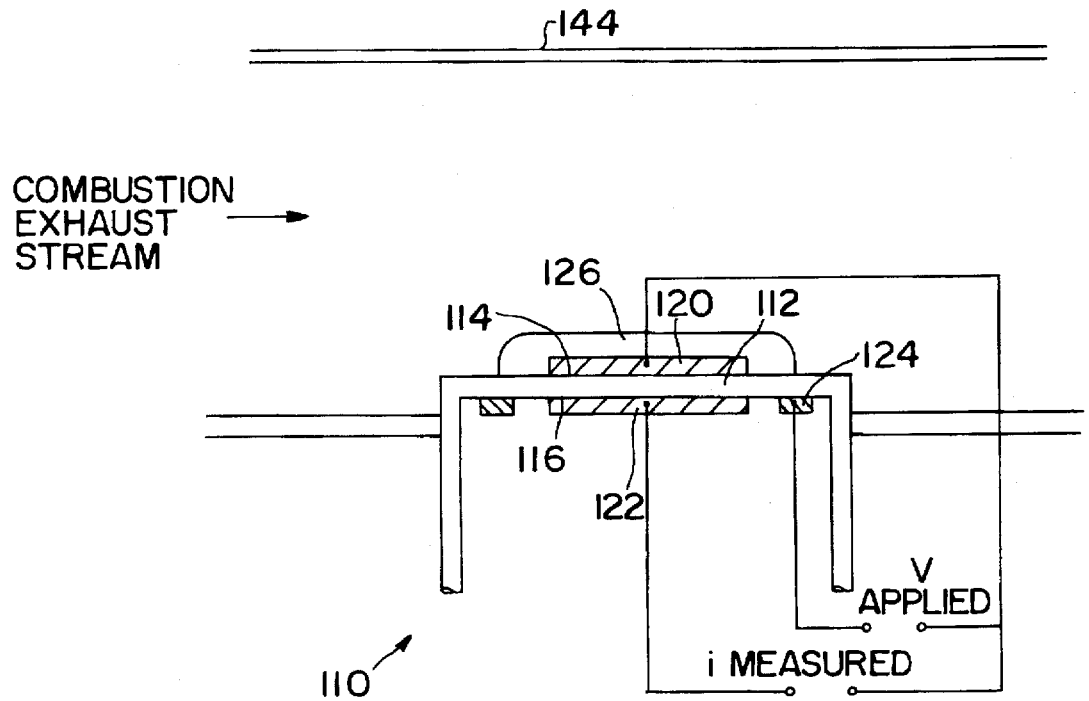
FIG. 2 is a schematic drawing of a multi-function sensor installed in fluid communication with the exhaust stream from a natural gas combustion system.

Referring to FIGS. 1 and 2, a multi-functional sensor 110 for a natural gas combustion system includes an ion-conductive electrolyte membrane 112 constructed from ceramic solid oxide material. The particular composition of the electrolyte membrane may vary according to the requirements of particular applications, and specific materials will be discussed later with regard to specific embodiments. Electrolyte membrane 112 has a fast surface 114 proximal the exhaust stream from a natural gas combustion system, and an opposing second surface 116 isolated from the exhaust stream. A sensing electrode 120 adheres to at least a portion of fast surface 114 of the electrolyte membrane, and a counter-electrode 122 adheres to a portion of the second surface 116. The sensing electrode includes a porous layer of catalytic material (e.g. a vanadia based material) atop a substrate made of fine particles of conductive material (e.g. palladium or platinum). The specific composition of both sensing and counter-electrodes 120 and 122 also may vary according to the requirements of particular applications, and will also be discussed later with regard to specific embodiments. A reference electrode 124 (made of e.g. platinum) may be adhered to the second surface 116 proximal the counter-electrode.

Sensing electrode 120 may be covered by a porous diffusion barrier 126 which limits the amount of exhaust gas that may diffuse to the sensing electrode. In a preferred embodiment, the diffusion barrier is constructed from the same material as the electrolyte membrane to eliminate complications from thermal expansion mismatches and to avoid chemical interactions. Alternatively, the diffusion barrier may be constructed from alumina. A laser bored diffusion aperture 128, typically less than 30 microns (µ) in diameter, establishes fluid communication between the exhaust stream and the sensing electrode 120. Methods other than laser boring, such as fiber-introduction during casting, may also be used to create the diffusion aperture.

In a preferred embodiment best illustrated by FIG. 1, an exhaust gas compartment 132 in fluid communication with the exhaust stream is disposed between diffusion barrier 126 and electrolyte membrane 112. Fluid access to the exhaust gas compartment may be had through diffusion aperture 128. The exhaust gas compartment allows exhaust gases entering through diffusion aperture 128 to diffuse out and contact a larger area of the sensing electrode 120. Exhaust gas compartment 132 is sealed around its edges to the diffusion barrier 126 and the electrolyte membrane 112 by glass seals 136 at the ends of ceramic spacers 138. Thus, the atmosphere inside the exhaust gas compartment is limited to exhaust gases that diffuse in through the diffusion aperture.

Sensing electrode 120, counter-electrode 122, and reference electrode 124 are electrically connected via electrical connection means 140 enabling a voltage potential indicated by reference letter V to be applied between the sensing electrode and the reference electrode. If no reference electrode is present, this potential is applied between the sensing and counter electrodes. The electrical connection means also enables an electrical current indicated by reference letter i to flow between the sensing electrode and the counter-electrode. Preferably, electrical connections are silver wire of 0.25 mm (0.01") in diameter, connected to the electrodes with a small amount of silver paste. The resulting connections may be fired at 500° C. for 30 minutes to set-up the silver paste, and bond the electrical connections to the electrodes.

In a preferred installation configuration best illustrated in FIG. 2, the sensor 110 is mounted in the wall 144 of the exhaust pipe from a natural gas combustion system. Exhaust gases from the exhaust stream are in fluid communication with the diffusion barrier 126, and thus free to diffuse through diffusion aperture 128 to sensing electrode 120, while both counter-electrode 122 and reference electrode 124 are isolated from the exhaust stream in a separate air atmosphere. Such a configuration is optional though, and the counter and reference electrodes may also be in fluid communication with the exhaust stream.

Figure 3:
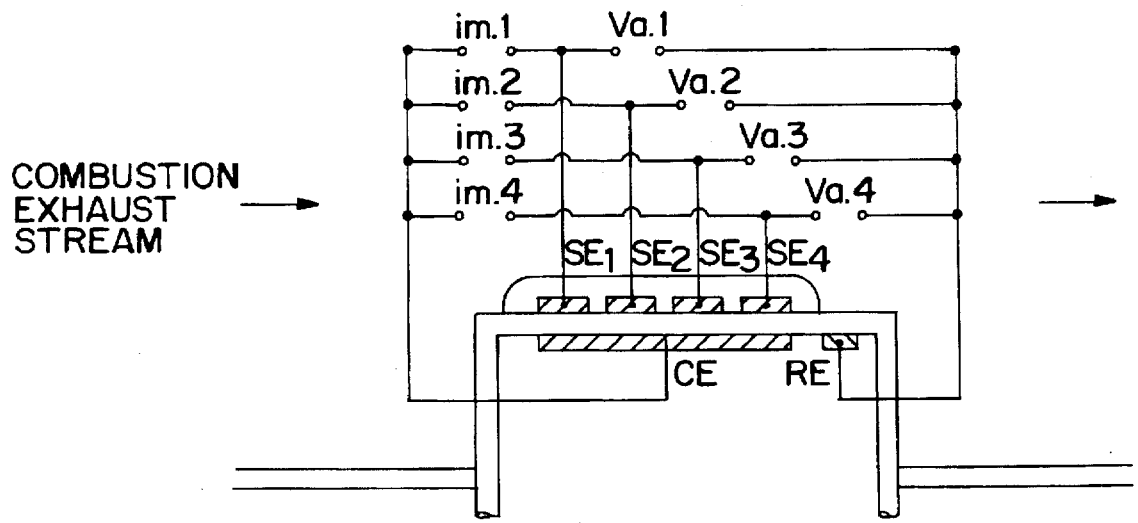
FIG. 3 is a schematic drawing of a multi-function sensor with multiple electrodes based on voltammetric principles for use in a control system for natural gas combustion systems.

Referring now to FIG. 3, a multi-electrode embodiment having a plurality of different sensing electrodes $SE_1$-$SE_4$ is schematically illustrated. Each sensing electrode may be constructed from a material having a high selectivity for a specific component in the exhaust gas stream. High selectivity to a chemical species results from specific adsorption of the chemical species at a catalyst. For example, the catalysts used for $NO_x$ sensors strongly adsorb $NO_x$ at the electrode surface, whereas other gas components in the mixture are physically inaccessible to the electrode. In this manner, sensors highly selective to, e.g. $NO_x$, CO, unburned hydrocarbons, and other combustion products can be constructed.

In operation, exhaust gases from the combustion system diffuse through diffusion aperture 128 into the exhaust gas compartment 132 where they contact the sensing electrode 120. In a sensor for oxygen-containing gases ($NO_x$, $CO_2$, $O_2$, CO, etc.), a negative voltage potential is applied to sensing electrode 120 with respect to reference electrode 124 which is exposed to air. In a sensor for hydrogen containing gases ($CH_4$, $H_2S$, and other hydrocarbons), a positive voltage potential is applied to sensing electrode 120 with respect to reference electrode 124 which is exposed to a hydrogen-containing atmosphere. The counter-electrode 122 in both cases may be exposed to air.

In the case of a sensor for oxygen-containing gases operating in voltammetric mode, when a negative potential sufficient to reduce an oxide to be sensed is applied to sensing electrode 120 (the cathode), the oxide is reduced, and the oxygen ions move through ion-conductive electrolyte membrane 112 to counter-electrode 122 (the anode) where they are oxidized to oxygen molecules in the air environment. In the case of a sensor for hydrogen-containing gases operating in voltammetric mode, when a positive potential sufficient to oxidize a hydrogen-containing chemical species to be sensed is applied to sensing electrode 120 (the anode), the species is oxidized, and the protons move through the electrolyte membrane to counter-electrode 122 (the cathode) where they are reduced to hydrogen molecules. Electrons involved in the redox reactions move from anode to cathode through electrical connection means 140 enabling measurement of an electrical current, the magnitude of which is proportional to concentration of the chemical species involved in the redox reaction.

Figure 4:
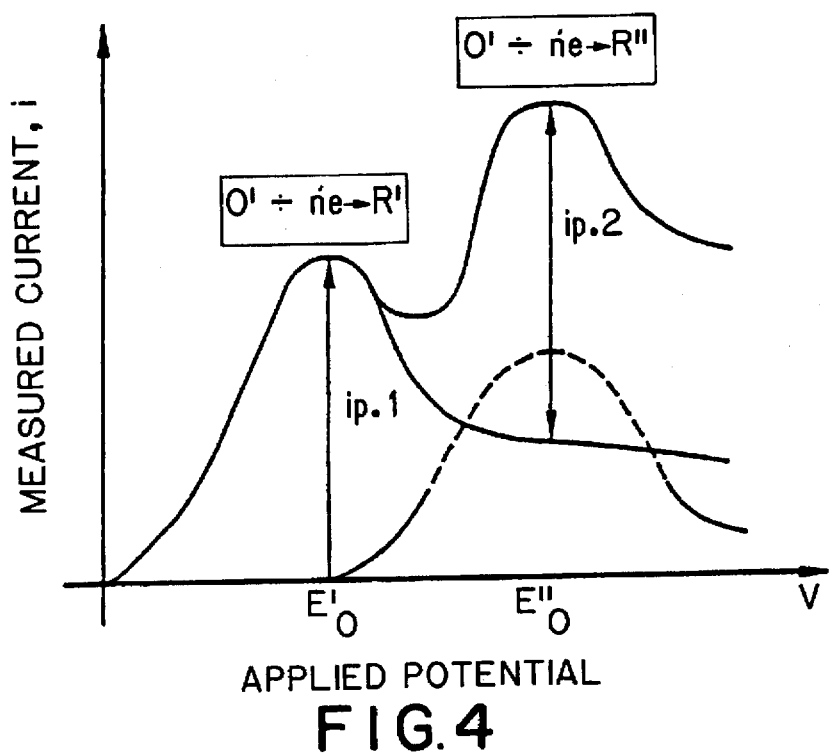
FIG. 4 is a steady state voltammogram of a mixture of two oxidizable species using the multi-function sensor according to the drawing of FIG. 1 under the condition that gas diffusion through the diffusion barrier is highly restricted.

In the voltammetric mode, sensor response is dependent upon the exhaust stream's flow pattern. The flow pattern can be regulated, however, by the configuration of diffusion barrier 126 and the pore size of diffusion aperture 128. Under the condition that exhaust gas diffusion through diffusion barrier 126 is highly restricted (i.e. a small diffusion aperture), the gas mixture near the surface of sensing electrode 120 will be barely convective. In this case, sensor response will show standard steady-state voltammetric waves with current peaks at discrete characteristic potentials associated with certain chemical species. For a multicomponent system, if the diffusion of each species is independent of concentration gradients of other species, the fluxes are additive and the i-E or i-t curves for the mixture are the sum of the individual i-E curves of each species as illustrated in FIG. 4. The peak currents for the subsequent species must be corrected using the decaying current of the previous wave as the baseline. Accordingly, a given chemical species can be distinguished by the characteristic potentials ($E_p$) at which current reaches a maximum while the species' concentration can be estimated from the peak current ($I_p$).

Figure 5:
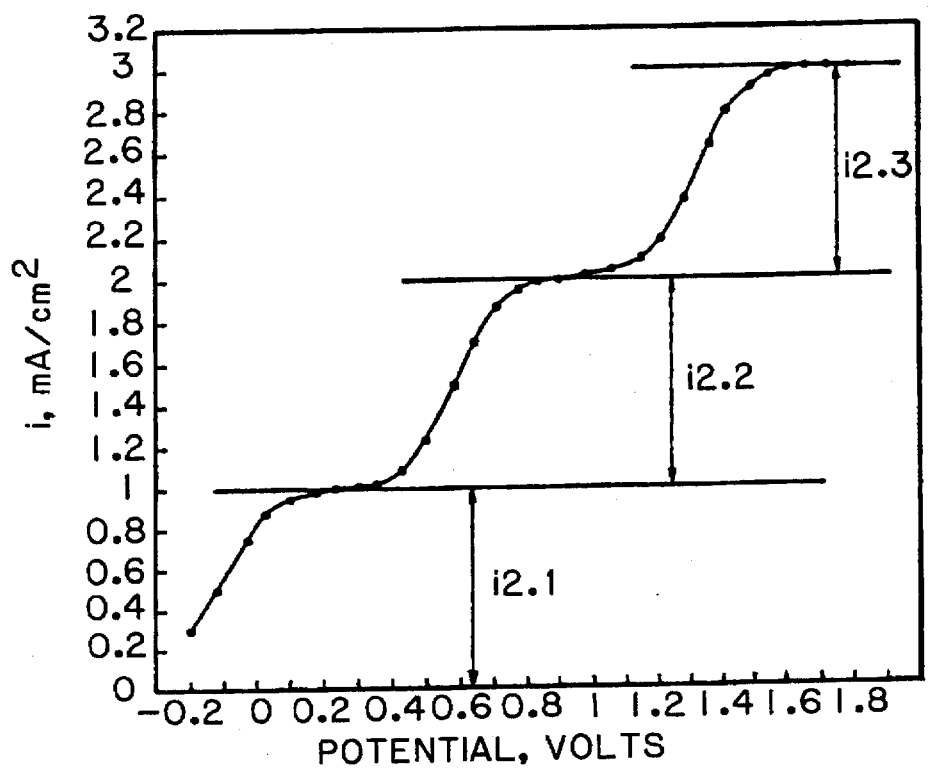
FIG. 5 is a steady state voltammogram of a mixture of three oxidizable species using the multi-function sensor according to the drawing of FIG. 1 under the condition that gas diffusion through the diffusion barrier is hardly restricted.

Under the condition that exhaust gas diffusion through diffusion barrier 126 is hardly restricted (i.e. a large diffusion aperture), the gas mixture near the surface of sensing electrode 120 will be finely convective. In this case, sensor response will show steady-state voltammetric waves under convective conditions, with current plateaus expected to occur in mass-transfer-limited regions. For a multicomponent system, if the subsequent process does not commence until the current plateau has been reached for the previous process, each component gas can be detected independently and distinguished by the potential at which the limiting current occurs as illustrated in FIG. 5. The concentration of each gas component can be estimated from the limiting current associated with the gas. Again, the limiting current for the subsequent process has to be corrected by subtracting the limiting current of the previous process.

In the case of a multi-function sensor having a plurality of different sensing electrodes such as illustrated in FIG. 3, each electrode has high selectivity for a specific gas component in the exhaust stream. Due to the fact that electrode kinetics can significantly shift the potential from the thermodynamic value at which redox reactions occur, this potential shift can be tailored by means of electrocatalysis to detect each gas component in the exhaust stream selectively. The high selectivity to a chemical species stems from the specific adsorption of the species at the catalyst. The sensor response is thus directly related to the surface coverage, while the gas concentration is obtainable from a suitable adsorption isotherm such as the Langmuir isotherm.

The composition of both ion-conductive electrolyte and electrode materials may be varied according to the requirements of particular applications. In principle, any suitable oxygen anion conductors can be used for oxygen containing gases, and, any suitable proton conductors can be used as electrolyte for hydrogen-containing gases. For example, zirconia-based ceramics such as tape-cast yttrium-strontium-zirconium (YSZ) with a thickness less than 0.2 mm, and thoria-based ceramics are suitable electrolyte materials for voltammetric sensors for oxygen containing gases. Isopressed pellets of $BaCeO_3$, and $SrCeO_3$ (yttria or Nd-doped) are suitable electrolyte materials for sensors for hydrogen and hydrocarbons. Electrode materials suitable for oxygen-containing gases include noble metals (Pt, Ag, Au, etc.), perovskites (LSM, LSCo, and modified LSM and LSCo, etc.), and other mixed oxides and transition metal sulfides and of mixture of them. Electrode materials suitable for reduction of $NO_x$, $SO_x$, $CO_2$, $H_2O$, as well as for oxidation of $H_2$, $CH_4$ and other unburned hydrocarbons include alumina-iron based catalysts, vanadia based catalysts ($V_2O_5/TiO_2$, $V_2O_5/Al_2O_3$, $V_2O_5/SiO_2$, etc.), nickel-based catalysts, and rare earth metals or other metal oxide based catalysts and the mixture of them. $V_2O_5$ based catalysts containing 50% of solid, which consists of 10 mol % of $V_2O_5$ and 90 mol % $TiO_2$ is a suitable catalyst for sensors detecting $NO_x$ and $O_2$.

The sensor can be operated in an amperometric mode whereby a steady electrical potential is applied to the sensor and the current response carries information about the chemical species undergoing reduction or oxidation. Amperometric sensors based on bismuth oxide-based ionic conductors have the attractive features of fast response (less than 30 seconds) and high sensitivity to oxygen, particularly in low concentrations.

The invention is further explained by the following illustrative examples.

EXAMPLE I

Figure 6:
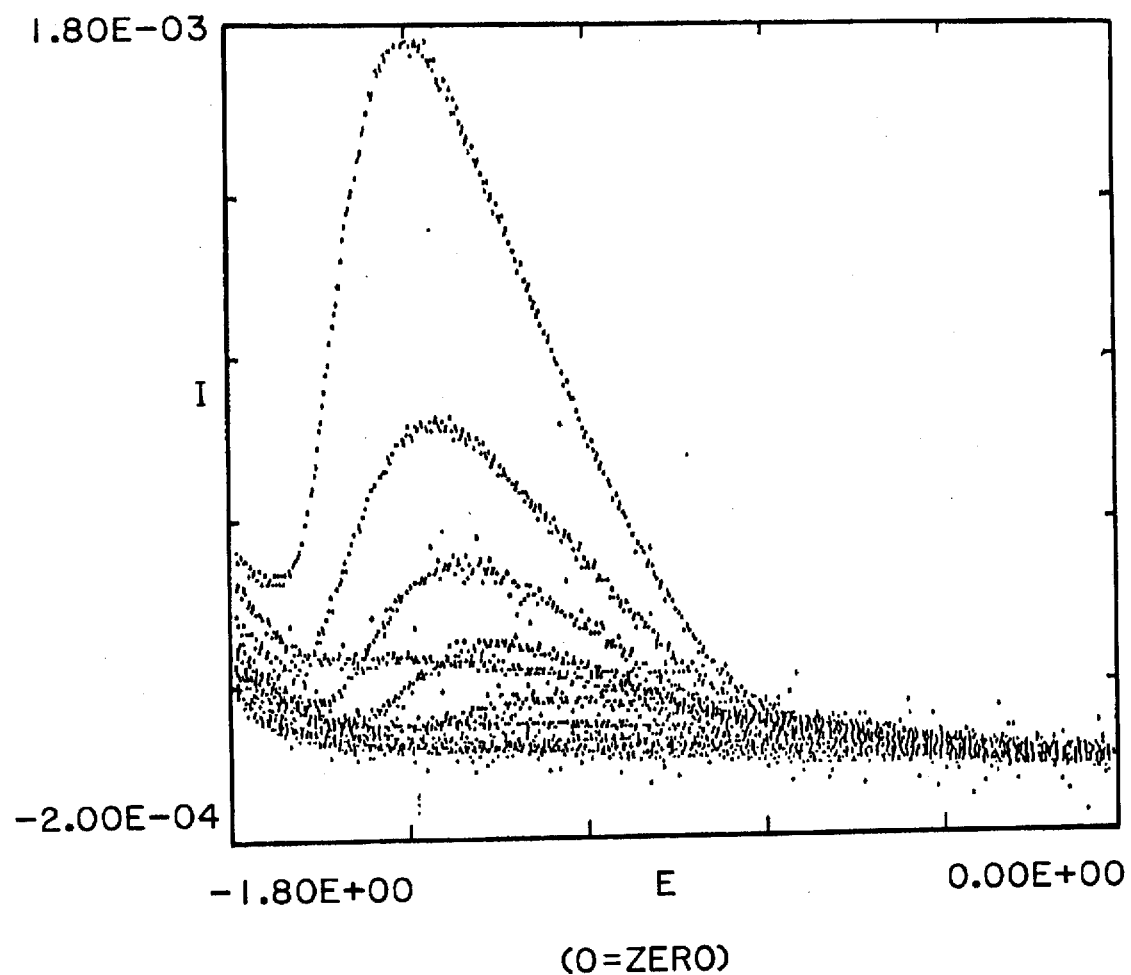
FIG. 6 is a cyclic voltammogram of a sensor in various concentrations of oxygen.

Several batches of voltammetric sensors were fabricated, arranged as per FIG. 1, having diffusion barriers made in different ways (laser-drilled and fiber-introduced holes) and having varying pore sizes (e.g. from 10 to 200 μm). Several typical voltammograms from these sensors are illustrated in FIG. 6 ($O_2$—$N_2$ mixture at 450° C. with a sweep rate of 100 mV/s).

Fabricated sensors were positioned in a quartz tube which was placed in a tubular furnace controlled at a constant temperature. Pre-mixed sample gases were flowed through the quartz tube at a controlled flow rate, typically from 60 to 150 cc/min. Each and every gaseous component in the mixture is adjustable individually.

A potentiostat/galvanostat (EG&G PAR 273) interfaced with a computer (IBM 286) was used to sweep the potential and to collect the current response of sensors under testing. The voltammograms were displayed on the computer screen after each potential sweep, and were recorded by a printer (FIG. 6).

Figure 7:
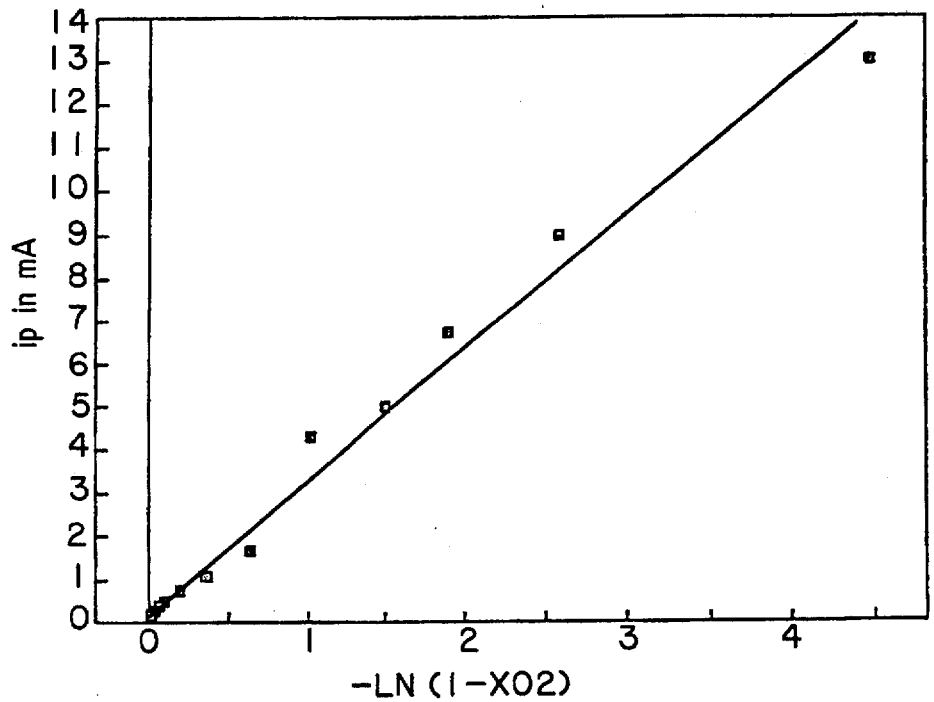
FIG. 7 is a plot of peak current as determined from cyclic voltammograms vs. oxygen concentration in the range from 0.1% to 99% that may be used as a standard curve.

A typical plot of peak current, as determined from cyclic voltammograms, versus oxygen concentration in the range from 0.1% to 99% is depicted in FIG. 7. Clearly, the peak currents, $i_p$, depend linearly on $-1\,n(1-X_{O2})$ over a wide concentration range, where $X_{O2}$ is the molar fraction of oxygen in the gas mixtures. This also indicates that the oxygen transports through the diffusion aperture by normal diffusion.

Figure 8:
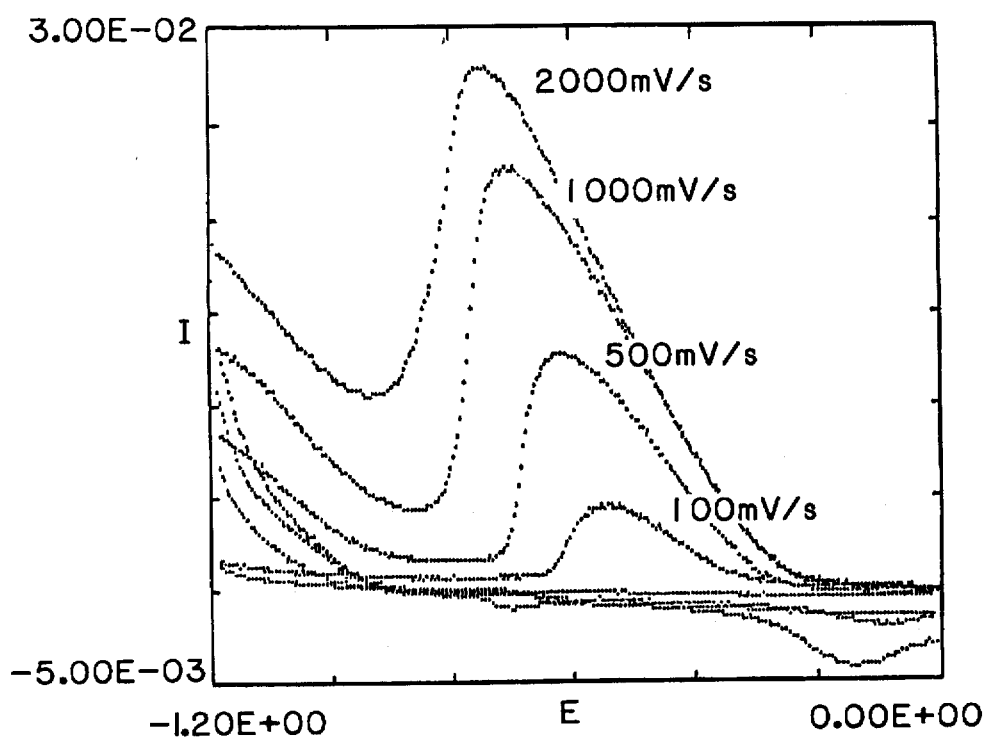
FIG. 8 is a cyclic voltammogram of a sensor in air at different sweep rates from 100 to 2000 mV/s.
Figure 9:
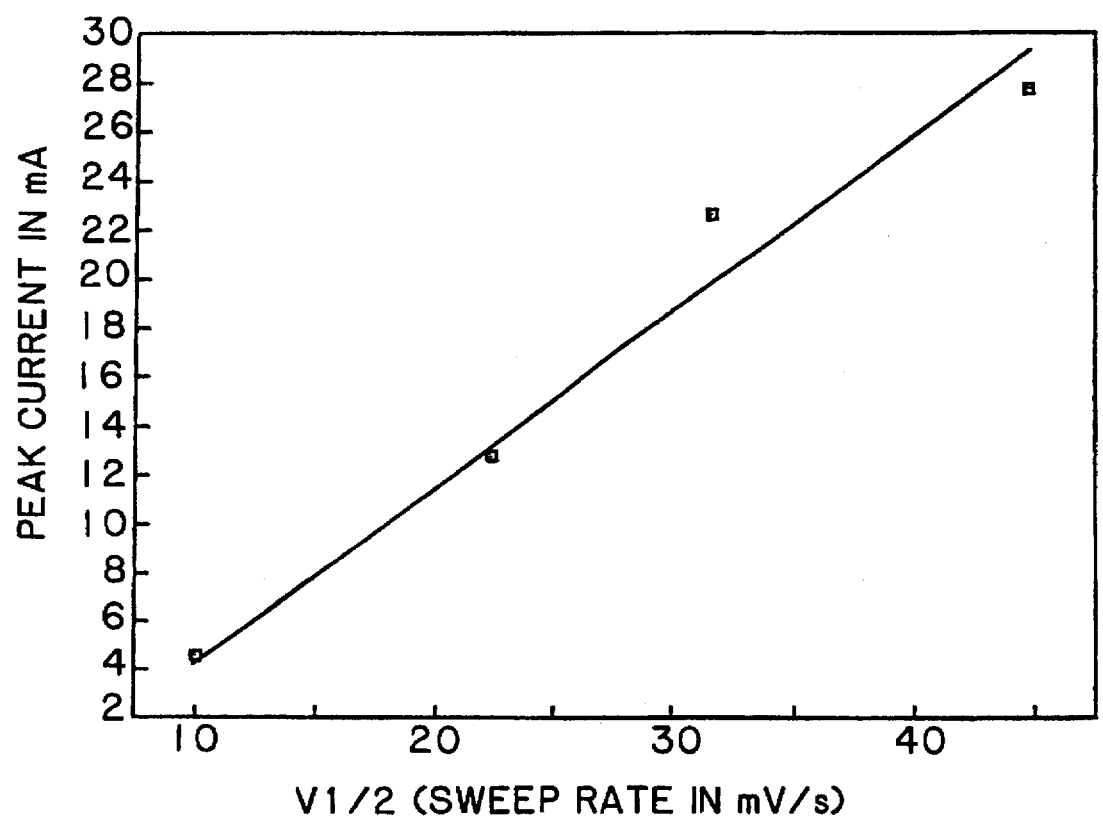
FIG. 9 is a plot of peak current vs. the square root of potential sweep rate in mV/s ($V^{1/2}$).
Figure 10A:
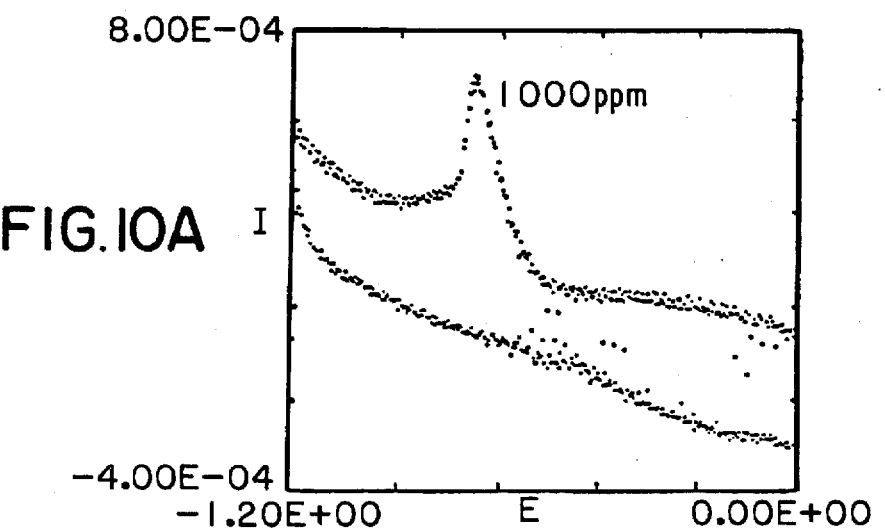
FIG. 10A is a cyclic voltammogram of a NO sensor in a gas mixture containing 1000 ppm NO.
Figure 10B:
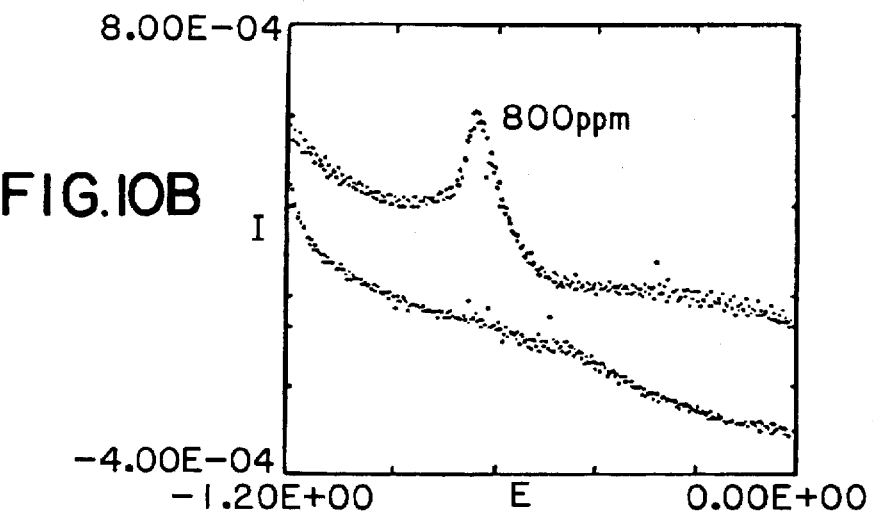
FIG. 10B is a cyclic voltammogram of a NO sensor in a gas mixture containing 800 ppm NO.
Figure 10C:
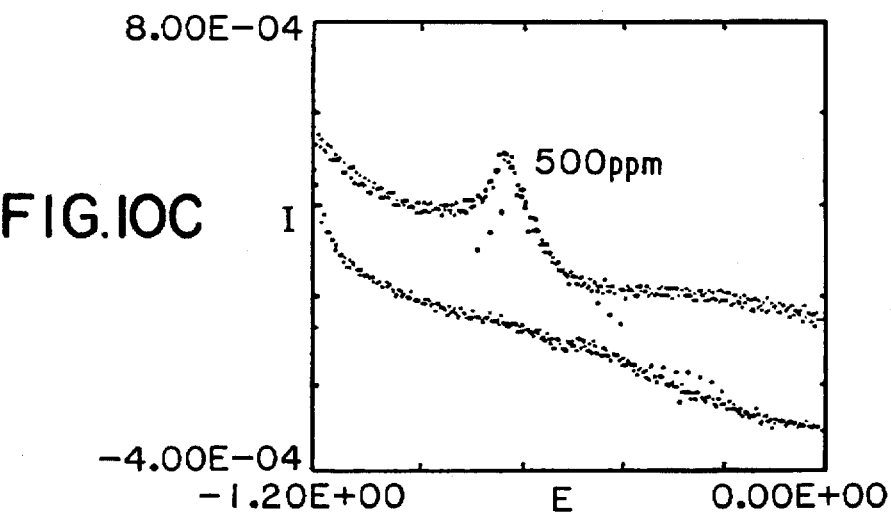
FIG. 10C is a cyclic voltammogram of a NO sensor in a gas mixture containing 500 ppm NO.

FIG. 8 contains some cyclic voltammograms of a sensor according to the invention in air at different sweep rates, from 100 to 2000 mV/s. The sharp current peaks for oxygen reduction at potential sweep rate of 2000 mV/s indicate that, in principle, this sensor is capable of generating a sensing signal in less that one second. In addition, as shown in FIG. 9, the peak current (mA) versus $V^{1/2}$ (square root of potential sweep rate in mV/s) of a voltammetric sensor according to the invention in air at 500° C. has a linear relationship, indicating that the reduction waves are in good shape.

Figure 11:
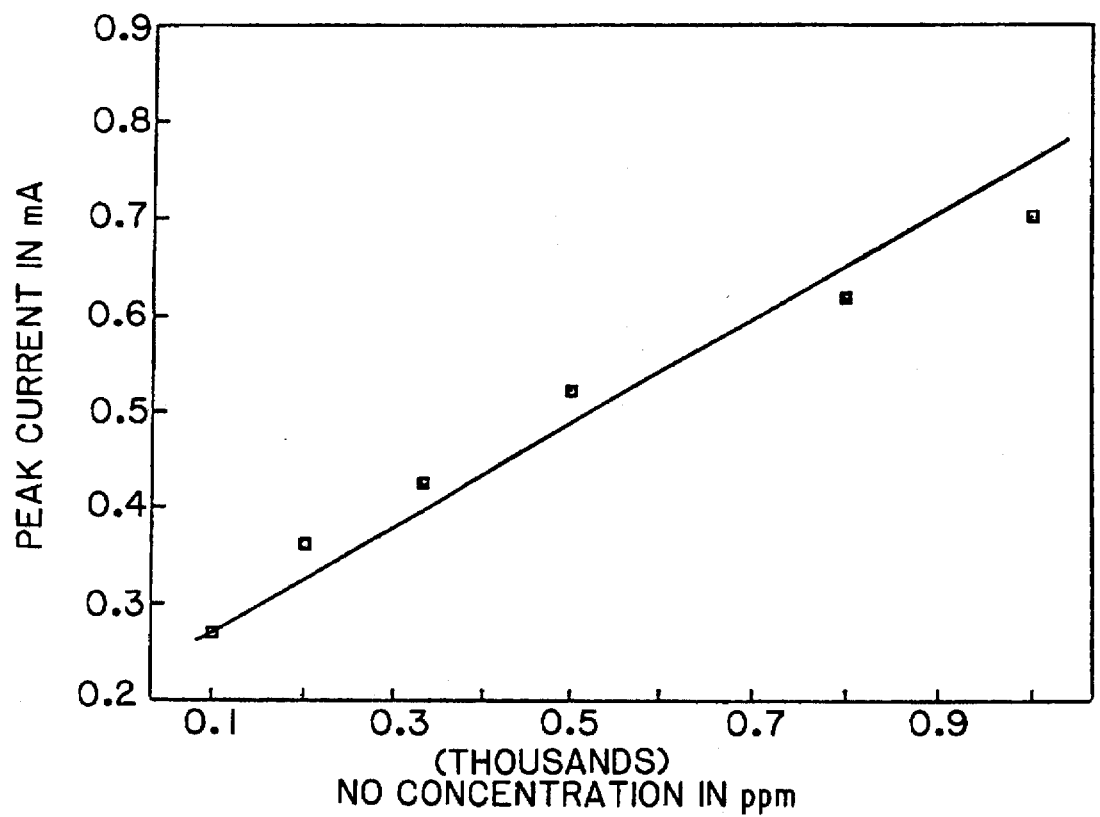
FIG. 11 is a plot of peak current vs. concentration of NO that may be used as a calibration curve.
Figure 12A:
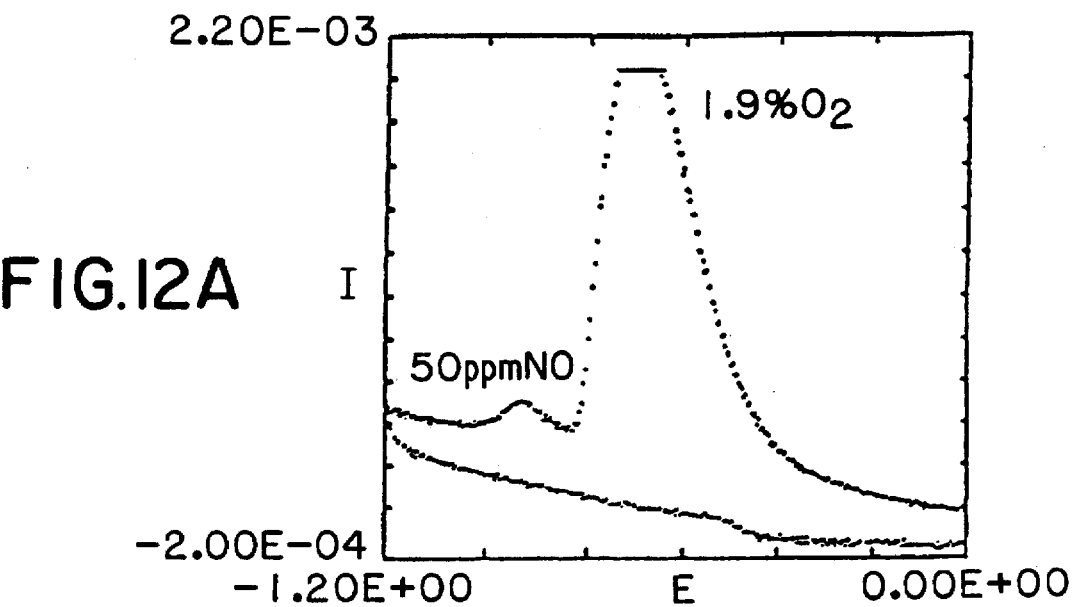
FIG. 12A is a cyclic voltammogram of a NO sensor gas mixture containing 500 ppm NO and 1.9% $O_2$.
Figure 12B:
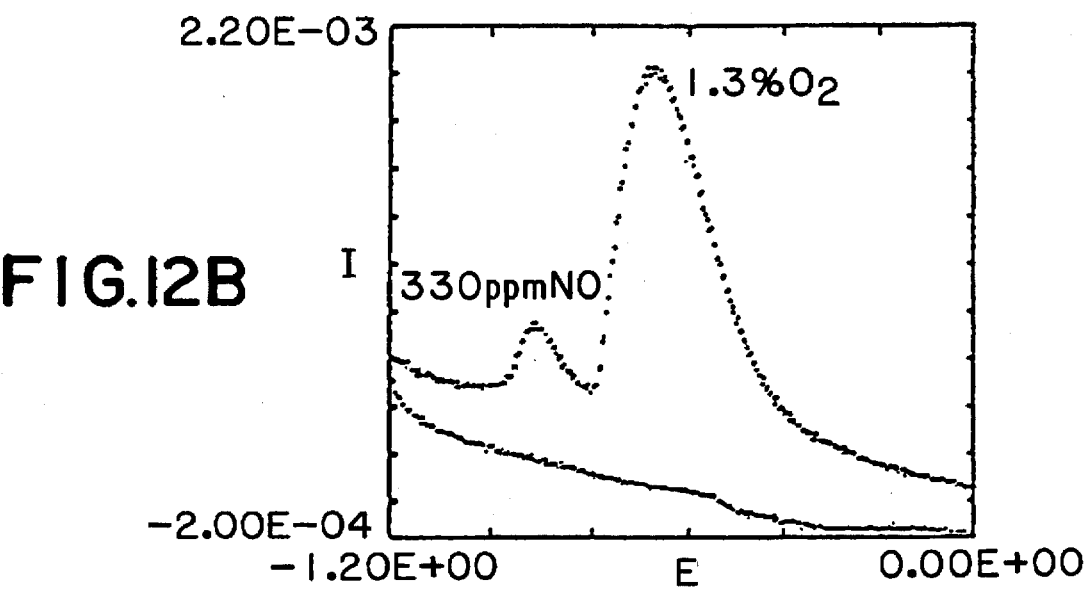
FIG. 12B is a cyclic voltammogram of a NO sensor an a gas mixture containing 330 ppm NO and 1.3% $O_2$.
Figure 12C:
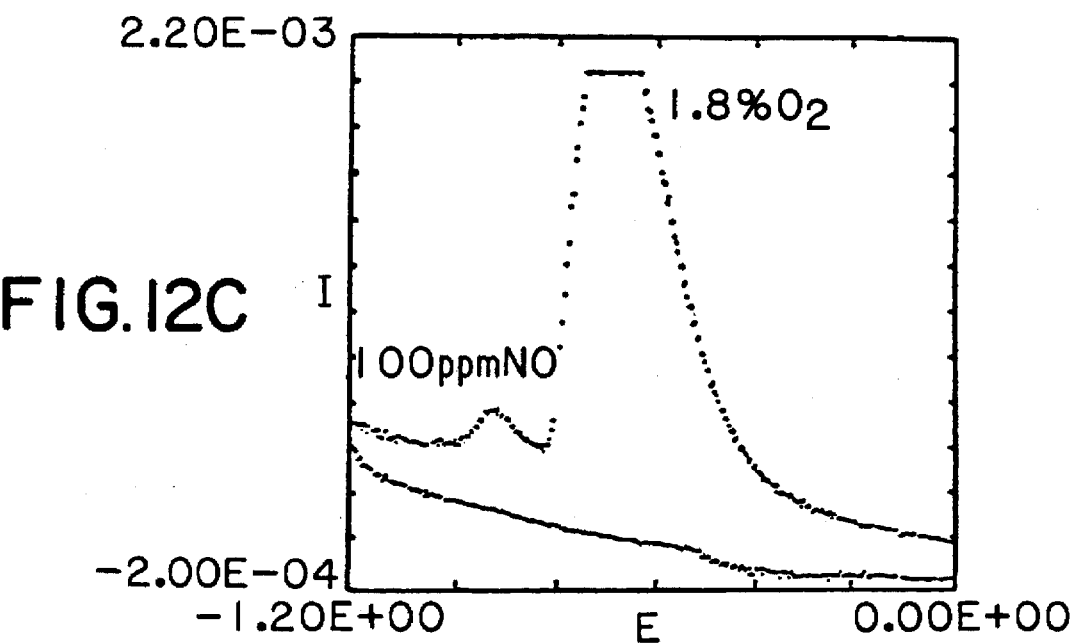
FIG. 12C is a cyclic voltammogram of a NO sensor an a gas mixture containing 100 ppm NO and 1.8% $O_2$.
Figure 12D:
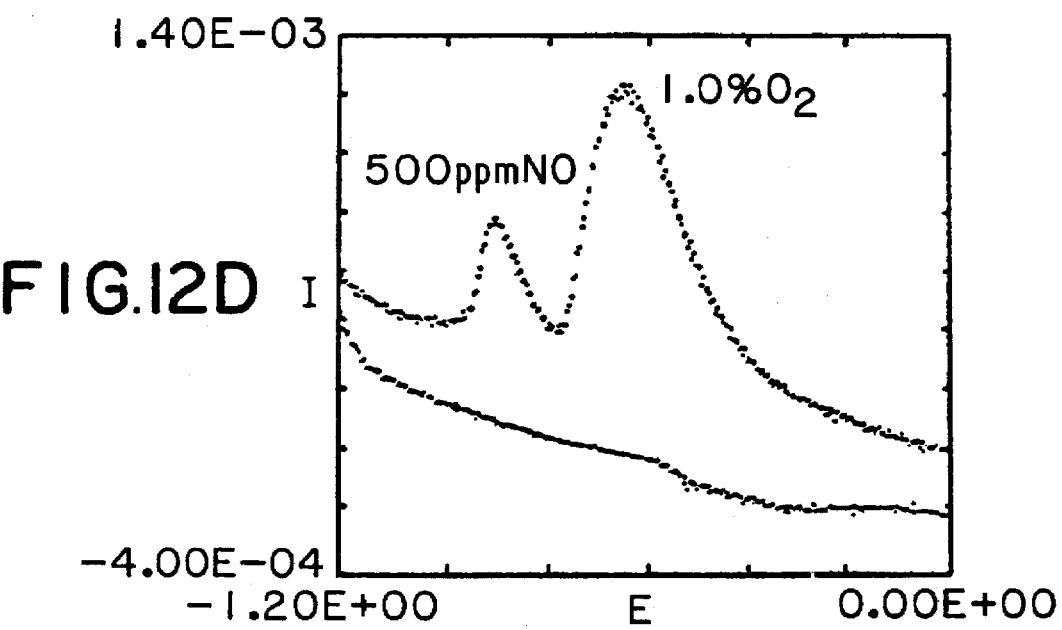
FIG. 12D is a cyclic voltammogram of a NO sensor an a gas mixture containing 500 ppm NO and 1.0% $O_2$.
Figure 13A:
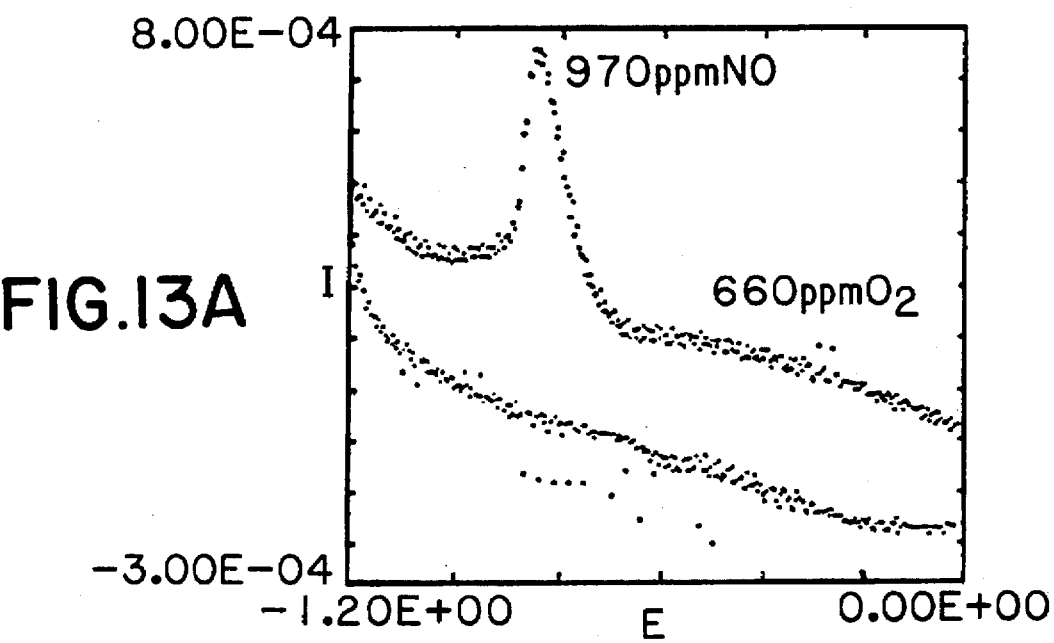
FIG. 13A is a cyclic voltammogram of a NO sensor an a gas mixture of 970 ppm NO and 660 ppm $O_2$.
Figure 13B:
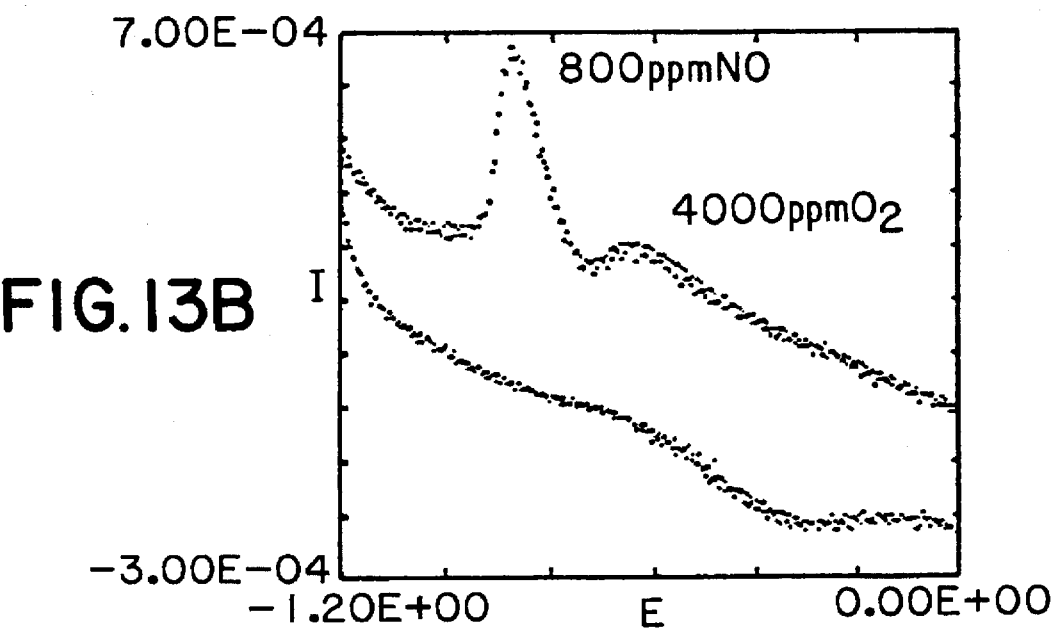
FIG. 13B is a cyclic voltammogram of a NO sensor an a gas mixture of 800 ppm NO and 4000 ppm $O_2$.
Figure 13C:
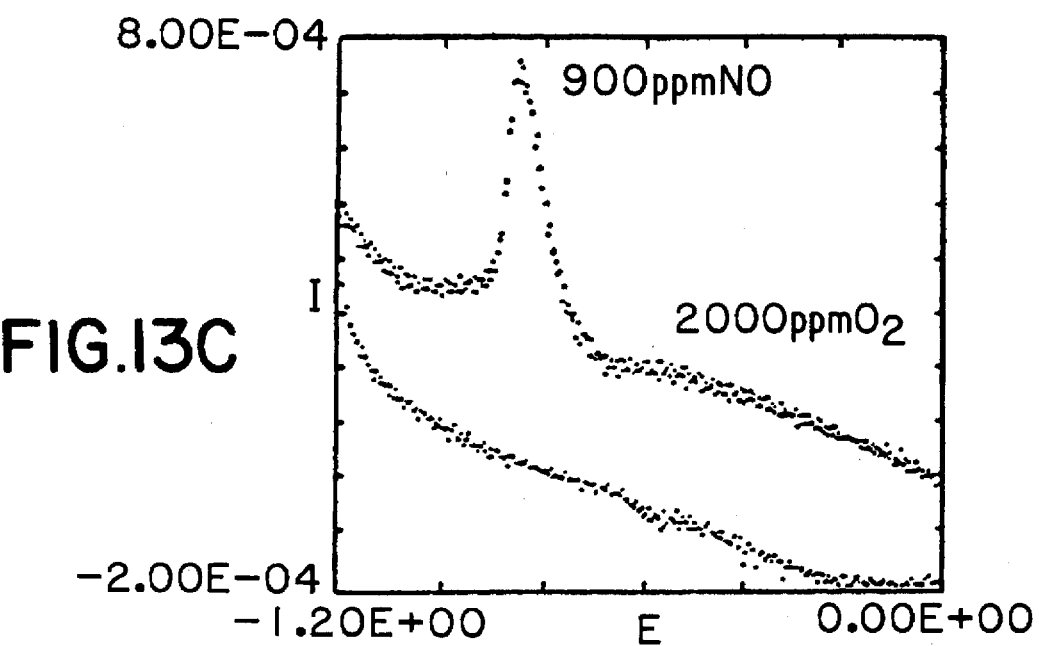
FIG. 13C is a cyclic voltammogram of a NO sensor gas mixture of 900 ppm NO and 2000 ppm $O_2$.
Figure 13D:
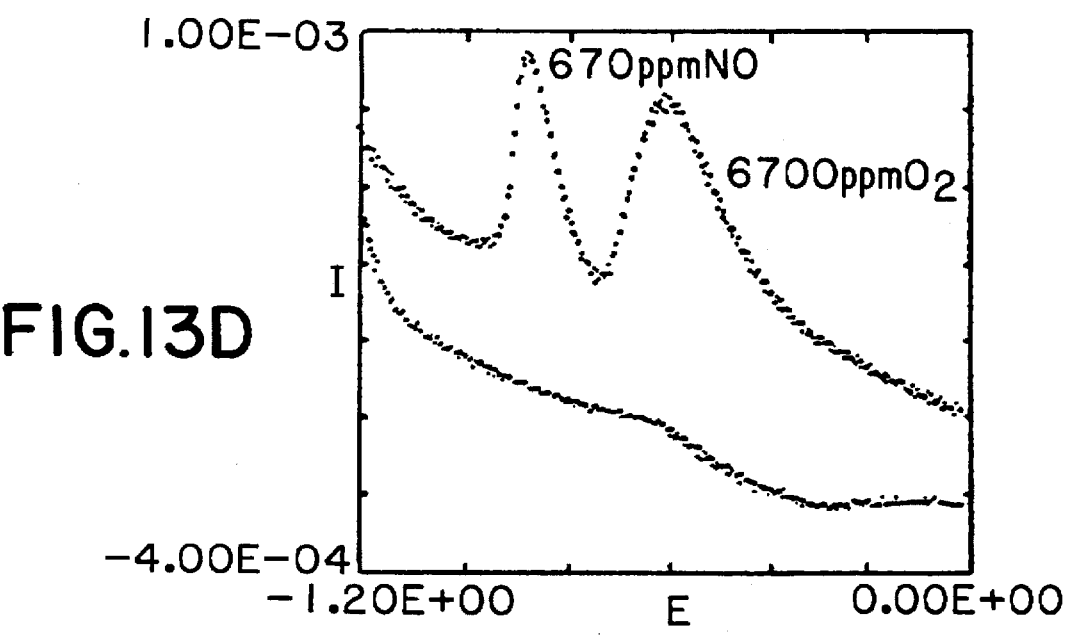
FIG. 13D is a cyclic voltammogram of a NO sensor gas mixture of 670 ppm NO and 6700 ppm $O_2$.
Figure 14A:
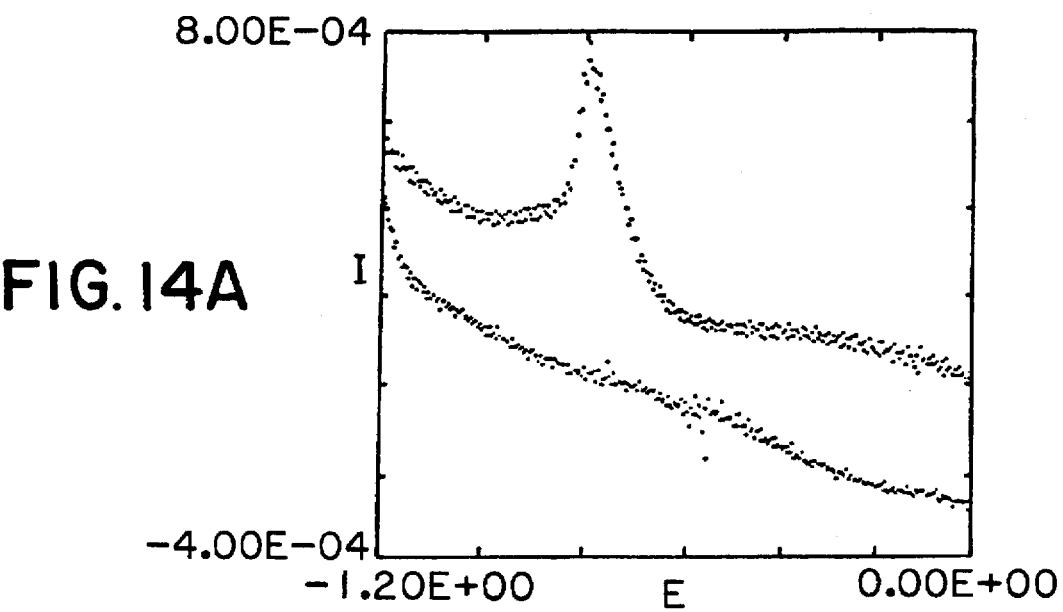
FIG. 14A is a cyclic voltammogram of a $NO_x$ sensor in an NO concentration of 1000 ppm and a sweep rate of 100 mV/s at 500° C.
Figure 14B:
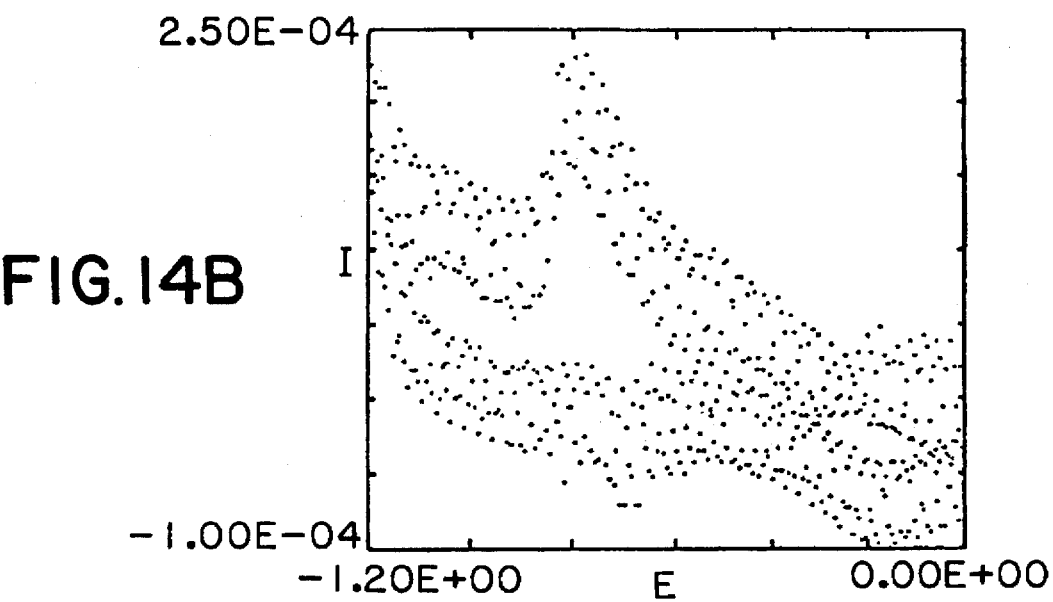
FIG. 14B is a cyclic voltammogram of a $NO_x$ sensor in an NO concentration of 1000 ppm and a sweep rate of 100 mV/s at 400° C.
Figure 14C:
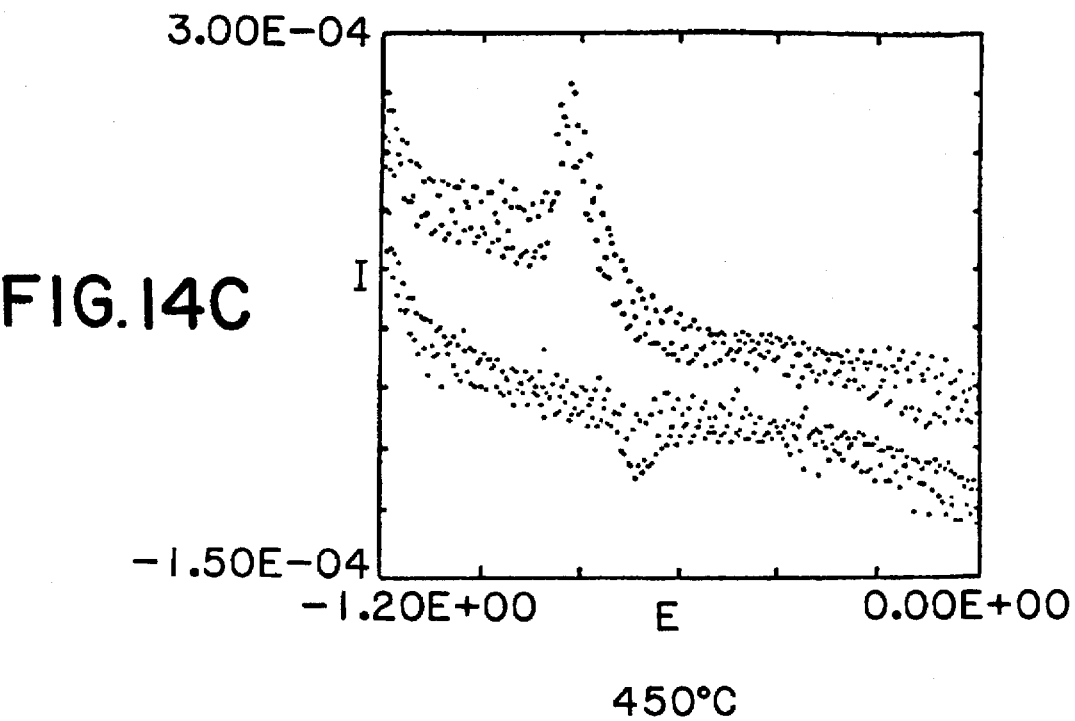
FIG. 14C is a cyclic voltammogram of a $NO_x$ sensor in an NO concentration of 1000 ppm and a sweep rate of 100 mV/s at 450° C.
Figure 14D:
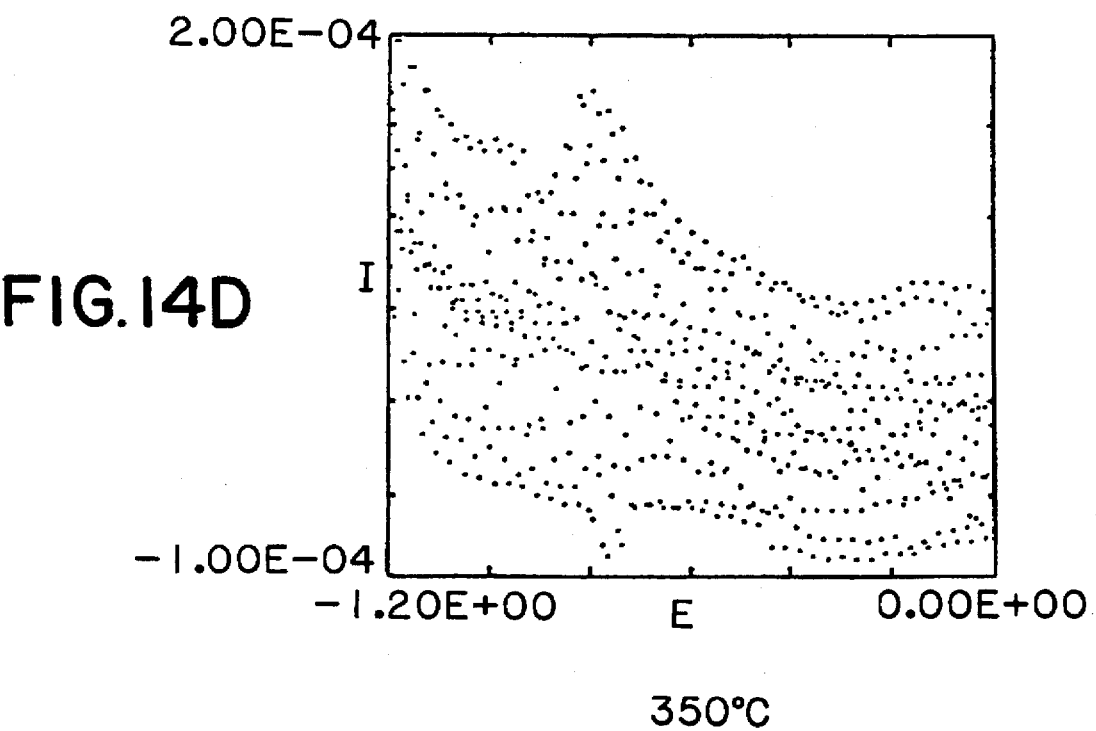
FIG. 14D is a cyclic voltammogram of a $NO_x$ sensor in an NO concentration of 1000 ppm and a sweep rate of 100 mV/s at 350° C.

FIGS. 10A–10E are typical voltammograms of a $V_2O_5$ coated NO sensor in gas mixtures containing different concentrations of NO at 500° C. and 100 mV/s. Clearly, the sensor responded to NO very well at about −0.8 V and peak current changed according to the concentration of NO. The linear relationship between peak current and concentration NO shown in FIG. 11 can be used as a calibration curve.

EXAMPLE II

Selectivity of Sensor

FIGS. 12A–12D and 13A–13D are voltammograms of a NO sensor in gas mixtures containing various concentrations of oxygen and NO. First of all, the sensor's selectivity to NO in a gas containing both NO and $O_2$ is about 10 times better than the selectivity to $O_2$. As shown in FIG. 1B, the response of the sensor to oxygen concentrations less than 2000 ppm is barely observable. Thus, when the concentration of $O_2$ is less than 2000 ppm, oxygen has no effect on detection of NO. Secondly, the reduction potential for oxygen is well separated from the reduction potential for NO so that NO can be detected in the presence of oxygen. For example, as shown in FIG. 12, the sensor's response to 50 ppm of NO is still observable even in the presence of 1.9% oxygen. Additionally, FIG. 6 shows that CO, $CO_2$, and hydrocarbons have no interference to the measurement of $O_2$ and NO.

EXAMPLE III

Temperature Dependence

Temperature dependence of peak current over the temperature range from 350° to 500° C. is shown in FIGS.

14A-14D. Clearly, as the operating temperature increases, the signal to noise ratio also increases.

EXAMPLE IV

Effect of Interfering Species

Figure 15A:
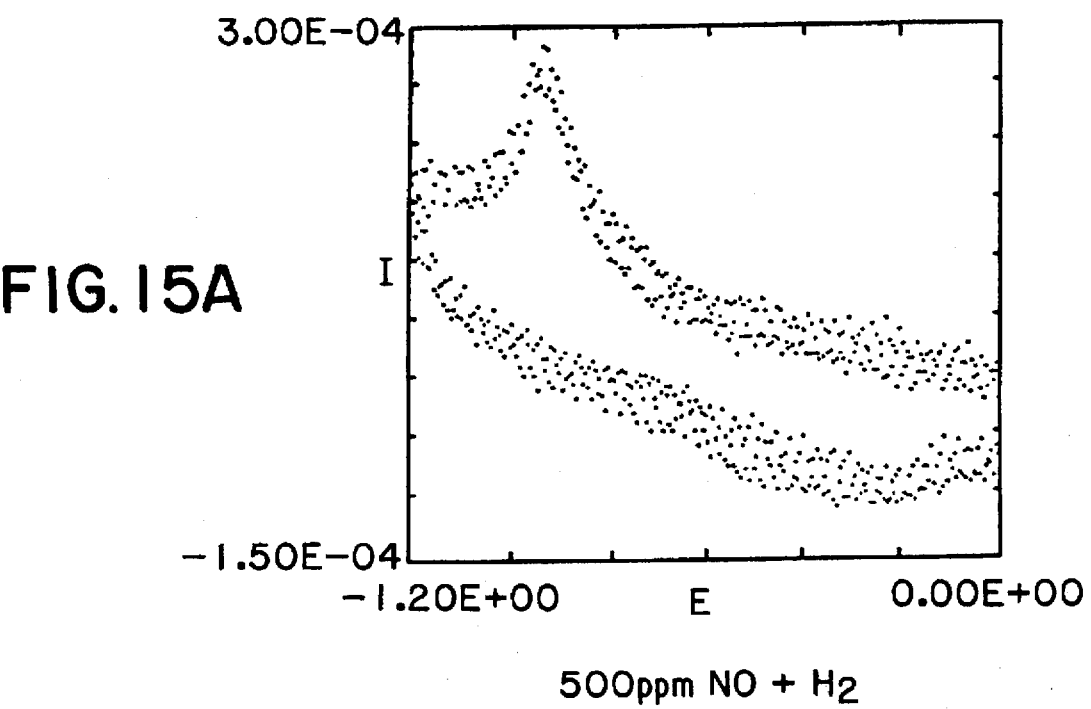
FIG. 15A is a cyclic voltammogram of a $NO_x$ sensor at 500 ppm NO with $H_2$ as an interfering species.
Figure 15B:
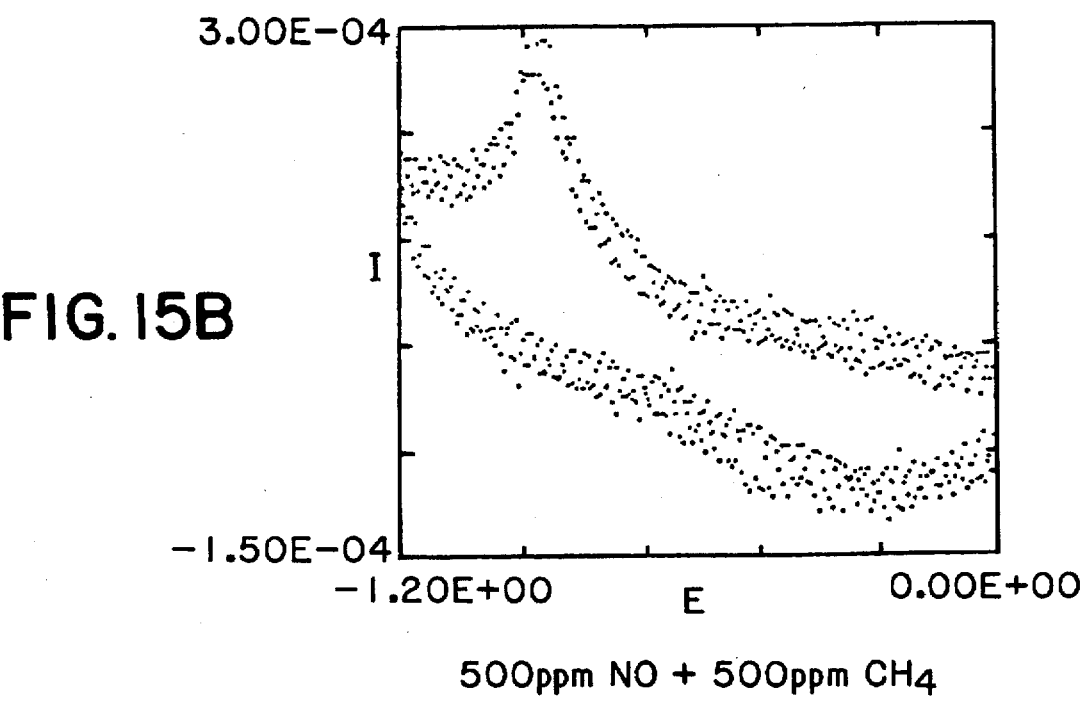
FIG. 15B is a cyclic voltammogram of a $NO_x$ sensor at 500 ppm NO with 500 ppm $CH_4$ as an interfering species.
Figure 15C:
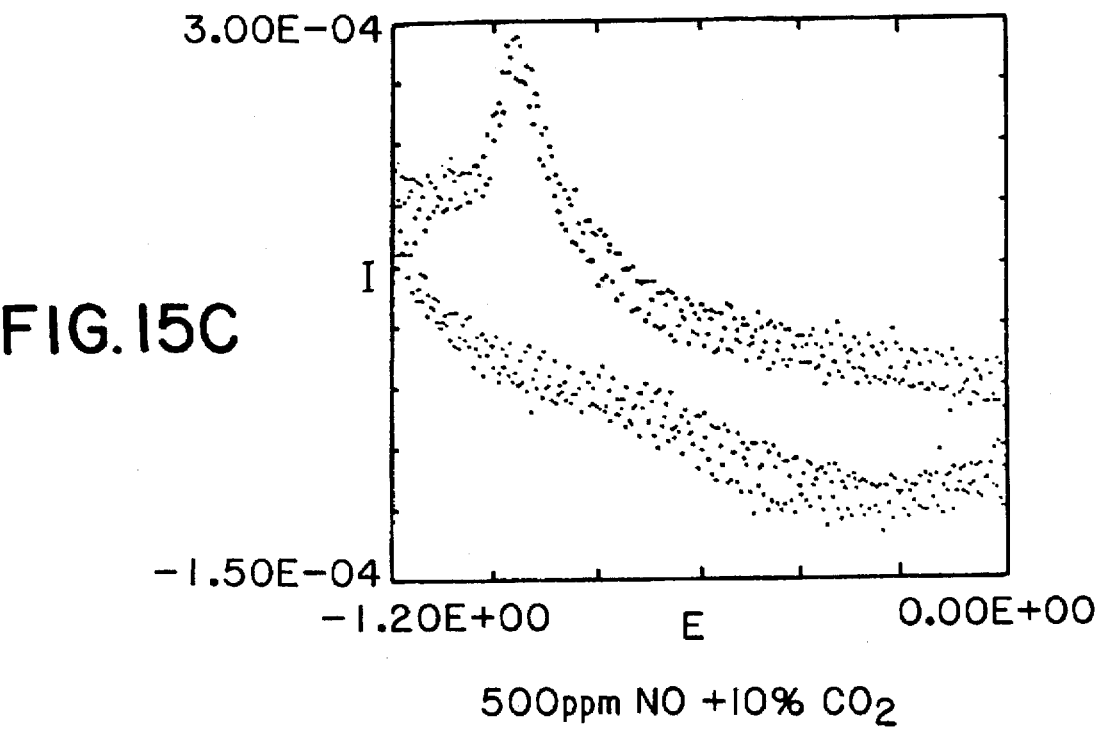
FIG. 15C is a cyclic voltammogram of a $NO_x$ sensor at 500 ppm NO with 10% $CO_2$ as an interfering species.
Figure 15D:
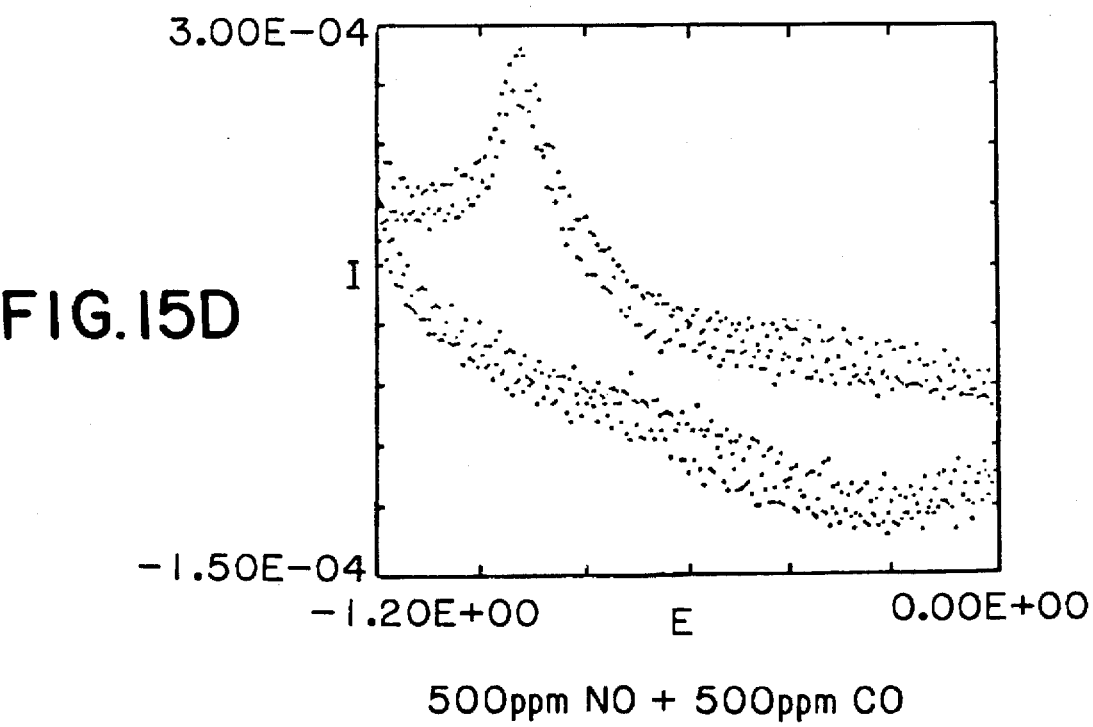
FIG. 15D is a cyclic voltammogram of a $NO_x$ sensor at 500 ppm NO with 500 ppm CO as an interfering species.
Figure 15E:
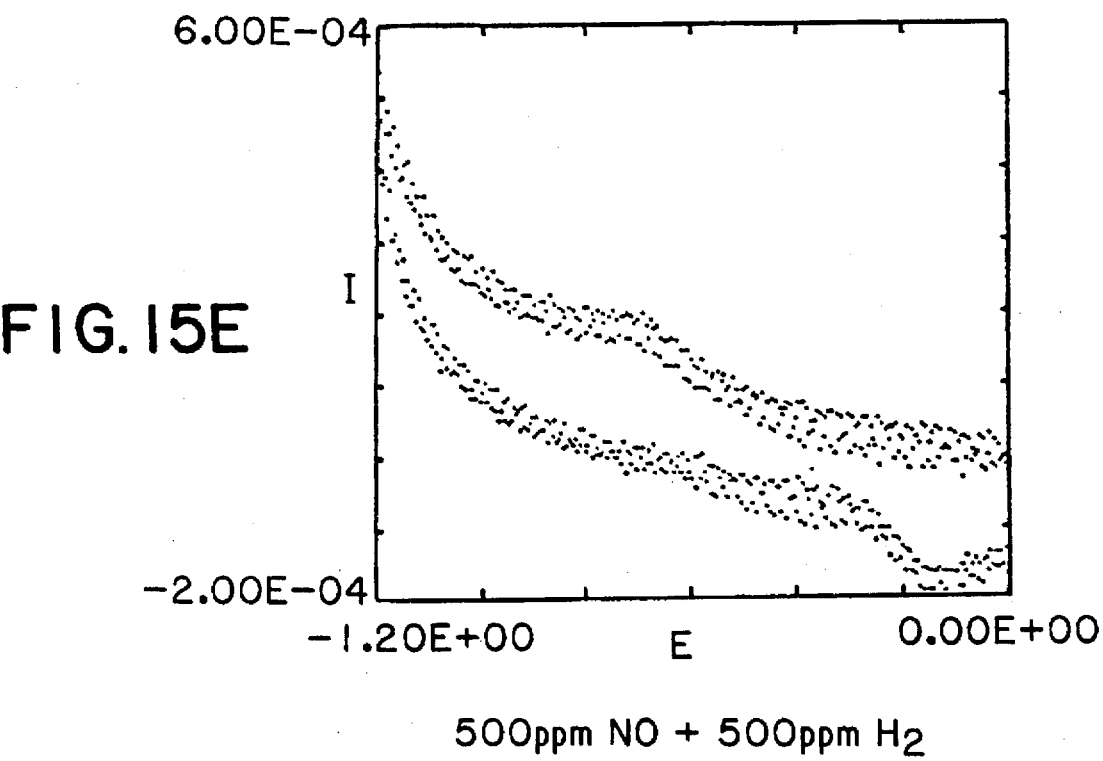
FIG. 15E is a cyclic voltammogram of a $NO_x$ sensor at 500 ppm NO with 500 ppm $H_2$ as an interfering species.
Figure 15F:
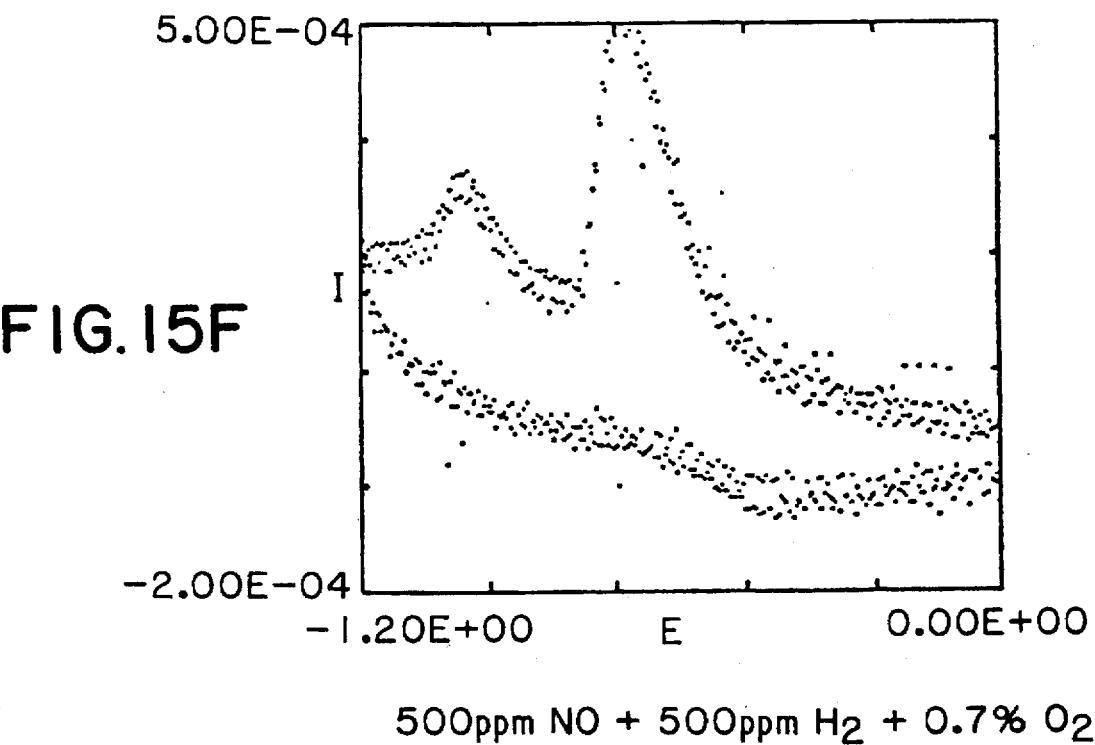
FIG. 15F is a cyclic voltammogram of a $NO_x$ sensor at 500 ppm NO with 500 ppm $H_2$ and 0.7% $O_2$ as interfering species.
Figure 16A:
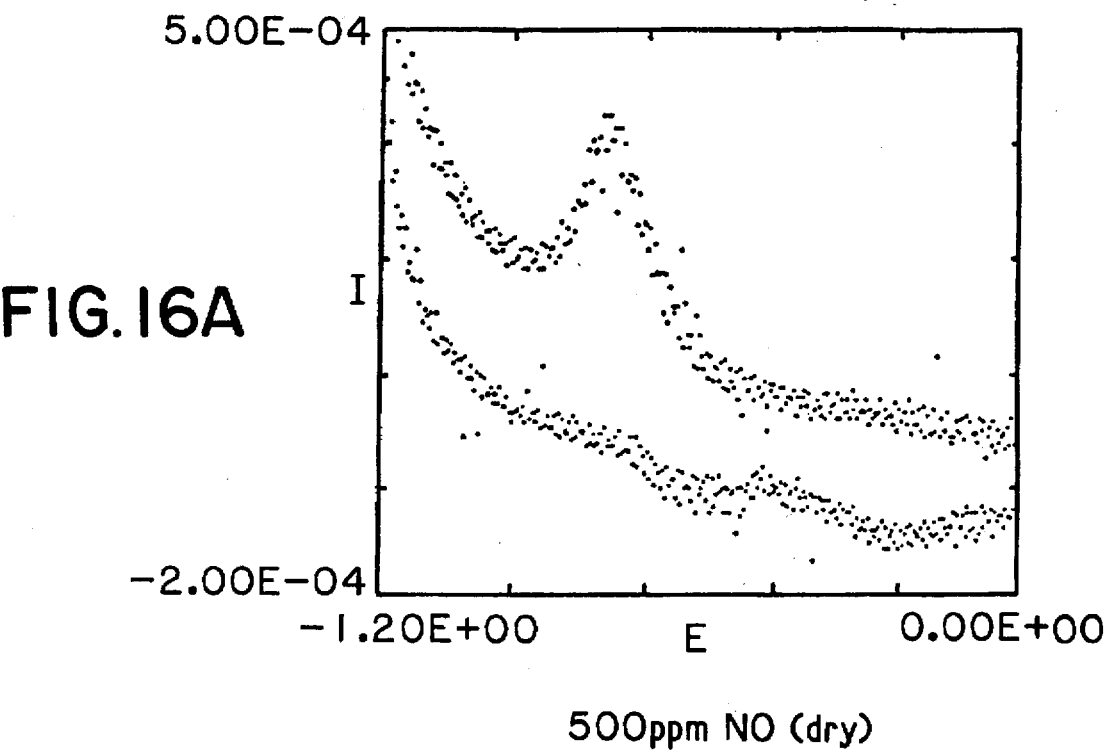
FIG. 16A is a cyclic voltammogram of a $NO_x$ sensor in 500 ppm NO with no $H_2O$ vapor.
Figure 16B:
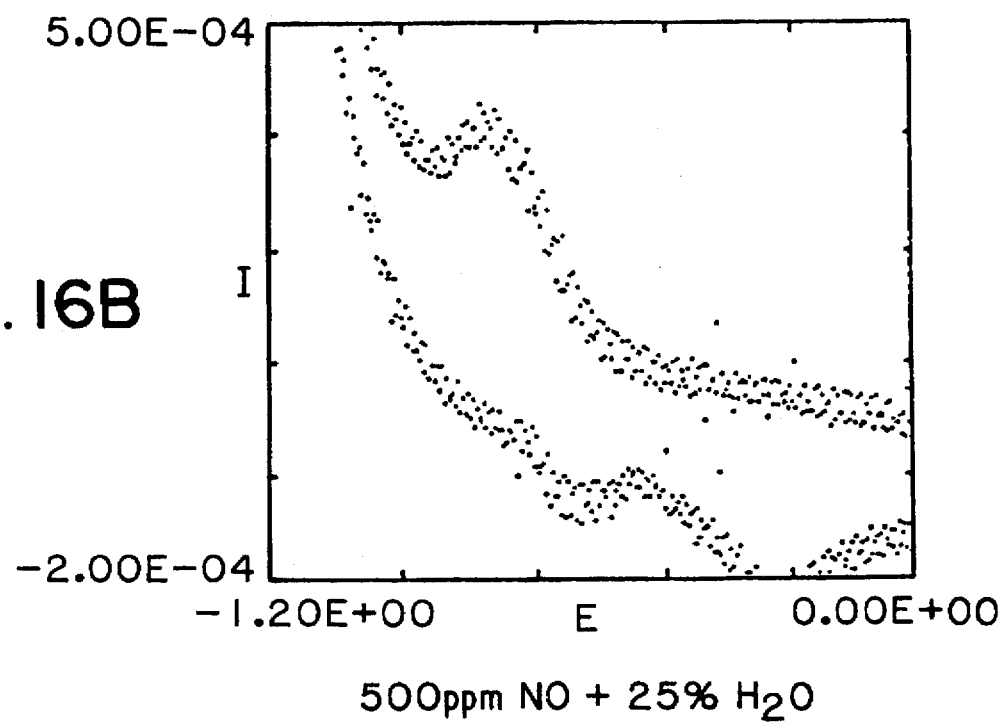
FIG. 16B is a cyclic voltammogram of a $NO_x$ sensor in 500 ppm NO with 25% $H_2O$ vapor.
Figure 17C:
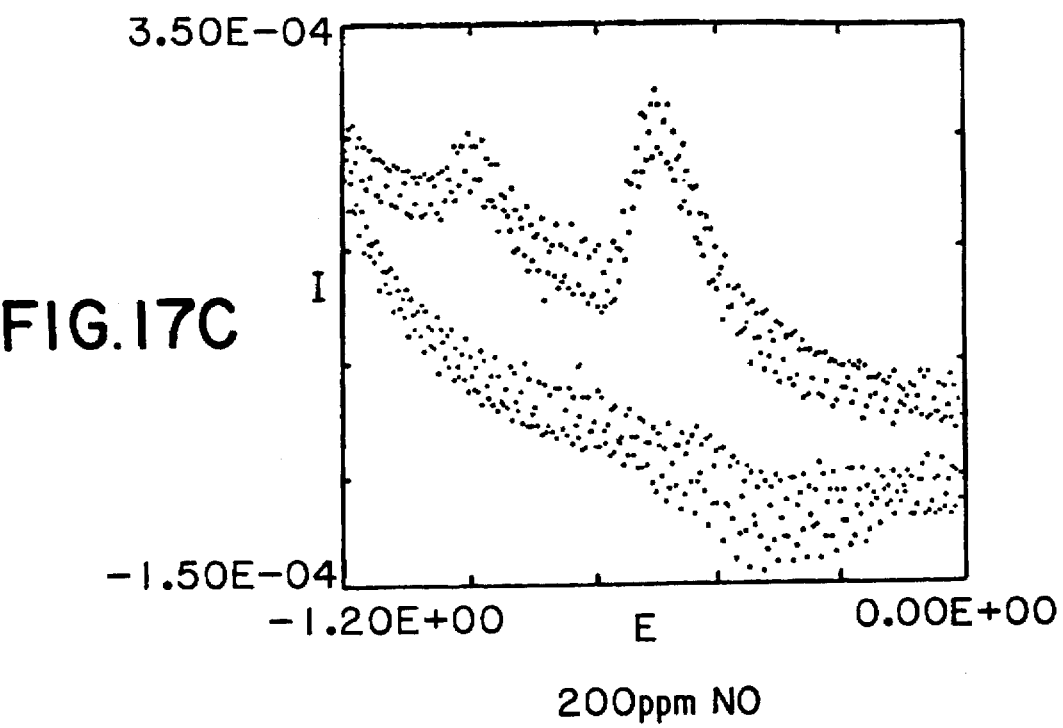
FIG. 17C is a cyclic voltammogram of a $NO_x$ sensor at 200 ppm NO with the same mixture of interfering species as in FIG. 17A and FIG. 17B.
Figure 17D:
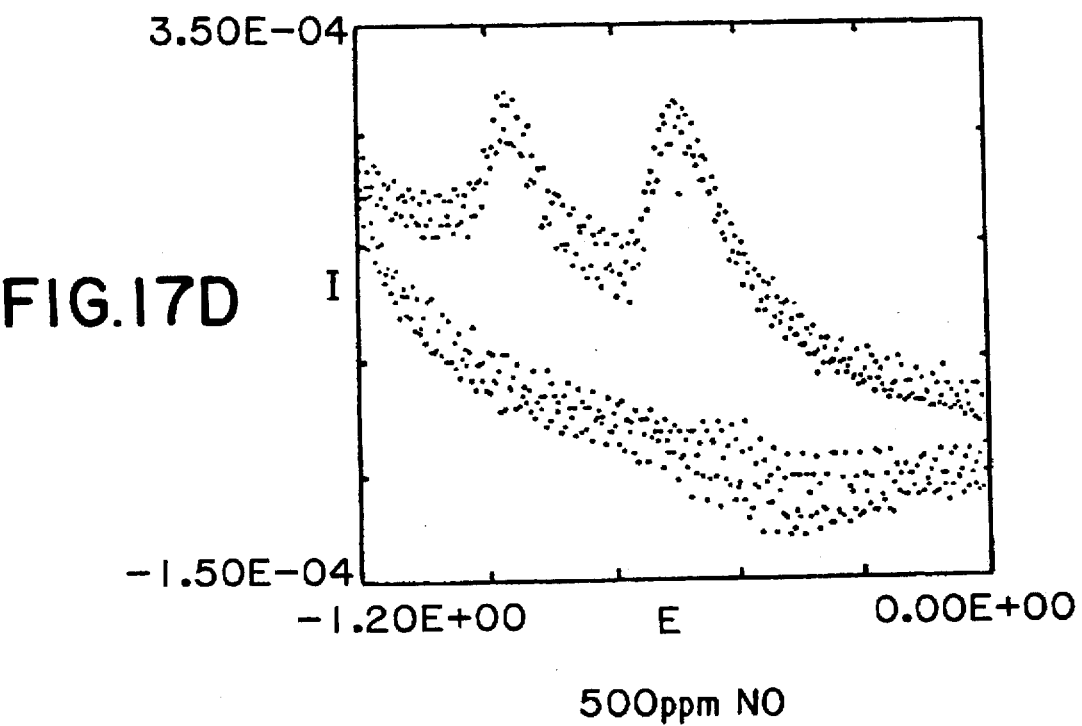
FIG. 17D is a cyclic voltammogram of a $NO_x$ sensor at 500 ppm NO with the same mixture of interfering species as in FIGS. 17A–17C.
Figure 18C:
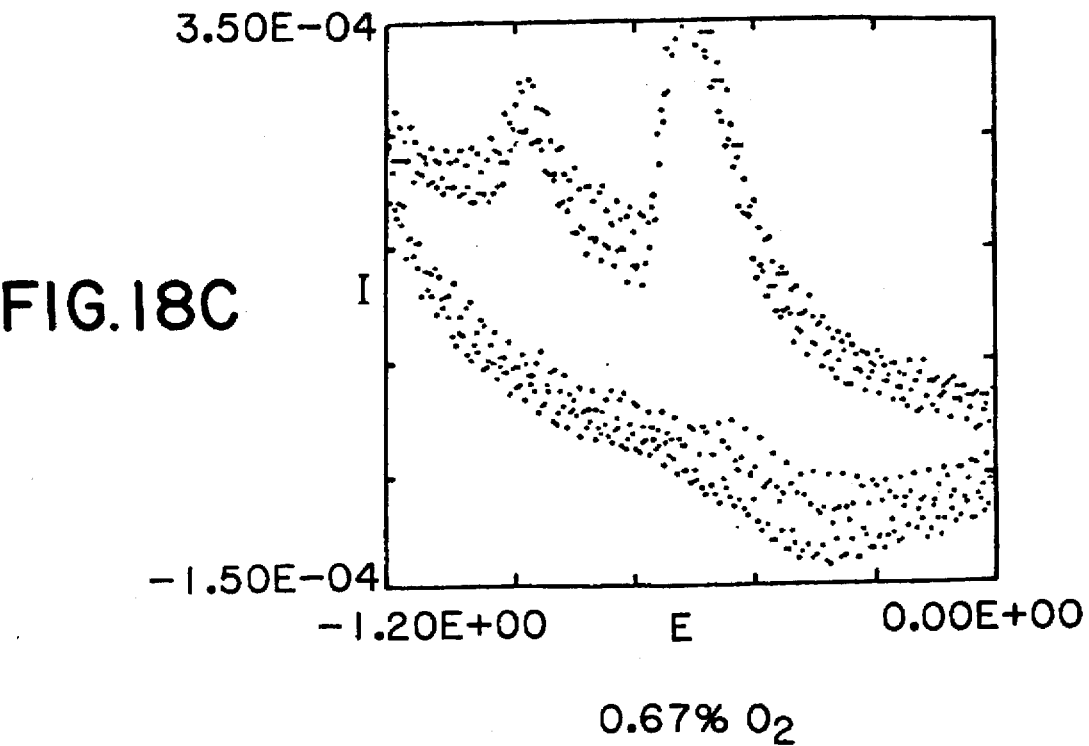
FIG. 18C is a cyclic voltammogram of the $NO_x$ sensor of FIGS. 18A and 18B, with the same concentration of NO, $CO_2$, $CH_4$ and $H_2O$, with 0.67% $O_2$.
Figure 18D:
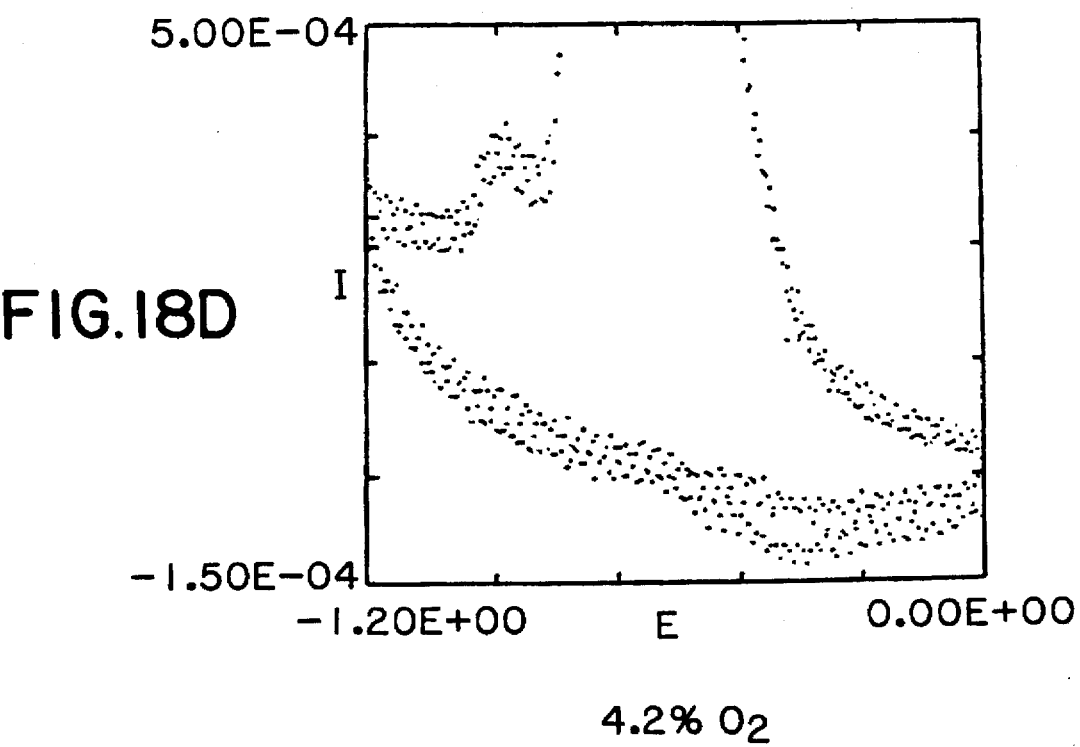
FIG. 18D is a cyclic voltammogram of the $NO_x$ sensor of FIGS. 18A–18C, with the same concentration of NO, $CO_2$, $CH_4$ and $H_2O$, with 4.2% $O_2$.
Figure 19A:
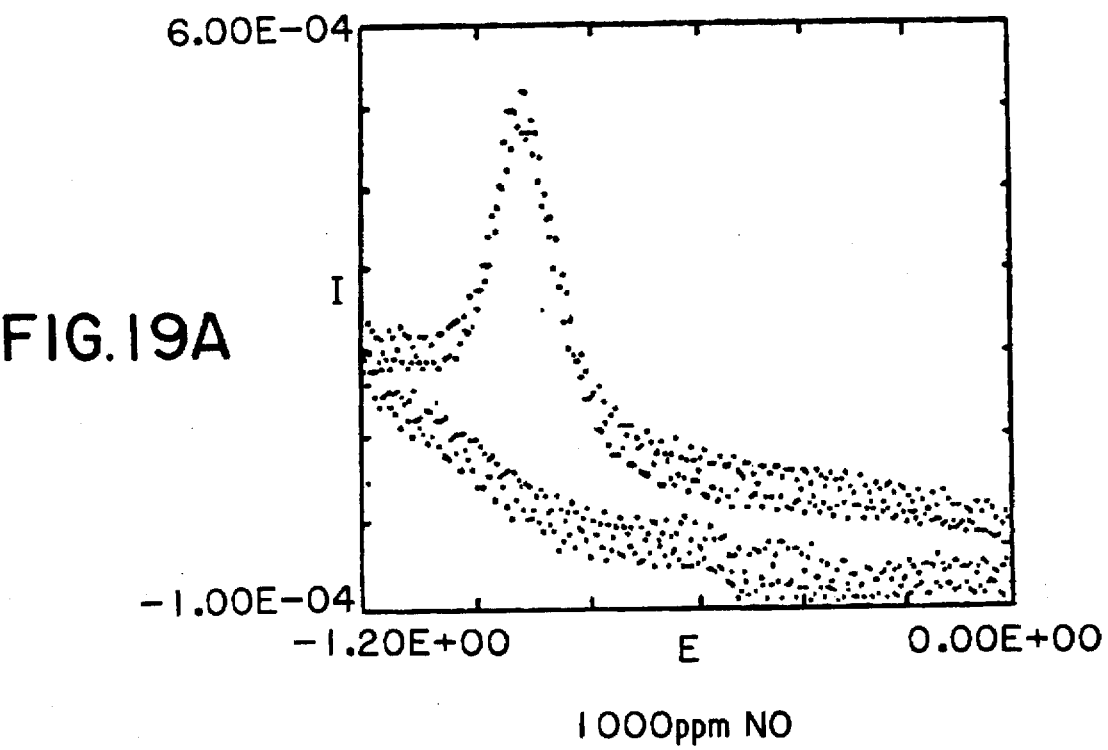
FIG. 19A is a cyclic voltammogram of a $NO_x$ sensor at 1000 ppm NO after storage in ambient atmosphere for 3 months.
Figure 19B:
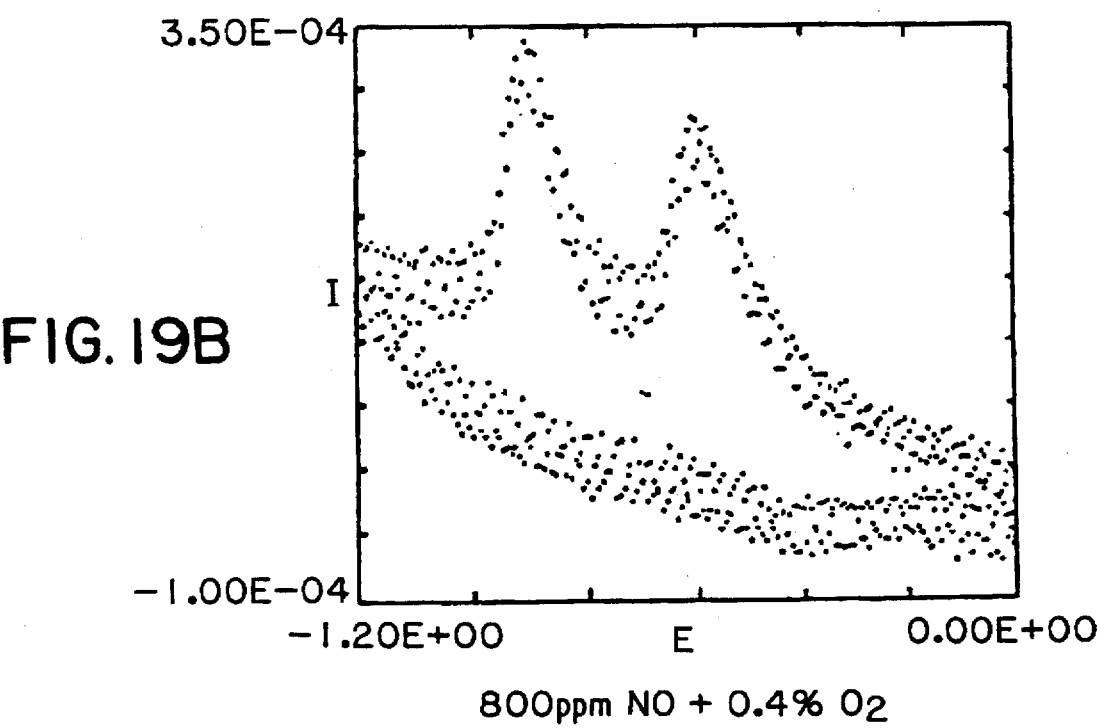
FIG. 19B is a cyclic voltammogram of a $NO_x$ sensor at 800 ppm NO and 0.4% $O_2$ after storage in ambient atmosphere for 3 months.
Figure 19C:
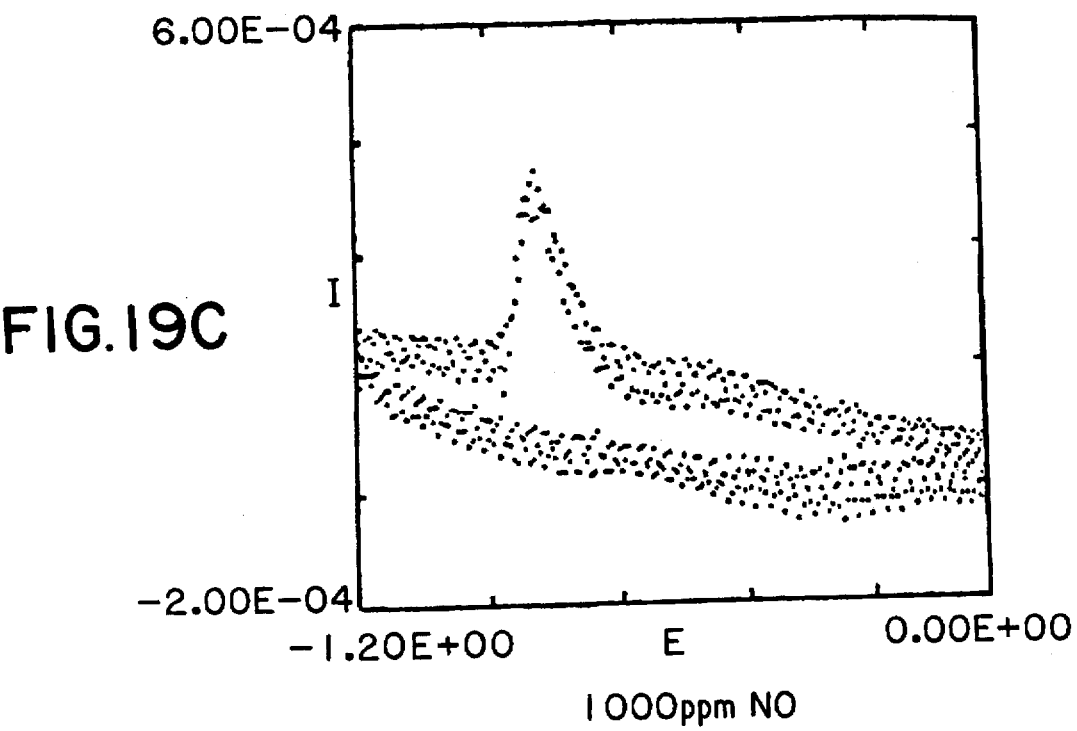
FIG. 19C is a cyclic voltammogram of a $NO_x$ sensor at 1000 ppm NO after storage in ambient atmosphere for 3 months.
Figure 19D:
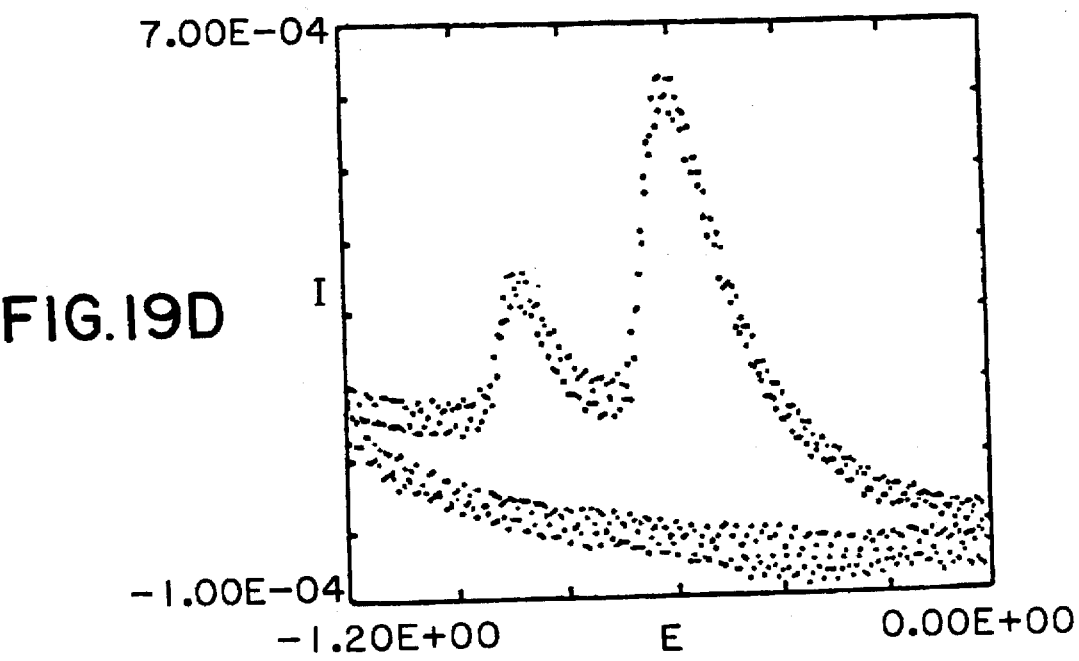
FIG. 19D is a cyclic voltammogram of a $NO_x$ sensor at 800 ppm NO and 0.4% $O_2$ after storage in ambient atmosphere for 3 months.

The effect of interfering species such as $CO_2$, $CH_4$, CO, $H_2$ and $H_2O$ to $NO_x$ sensors was studied individually. Voltammograms were taken after one hour of introduction of interfering species to gas mixtures. As shown in FIGS. 15A-15D, sensor performance was barely affected by adding 10% $CO_2$, 500 ppm $CH_4$ and 500 ppm CO gases into 500 ppm $NO_x$ gas. The existence of 500 ppm hydrogen, however, showed significant effect on the sensor's response to $NO_x$ as shown in the top frame of FIGS. 15E and 15F. One plausible explanation could be that the hydrogen introduced reacted directly with the $NO_x$ in the sample gas. Fortunately, the effect of hydrogen on sensor response to $NO_x$ was eliminated by introducing a small amount (0.7%) of oxygen into the gas mixture, as shown in the bottom frame of FIG. 15B. Since a small amount of oxygen is present in an actual combustion system exhaust, the effect of hydrogen on sensor performance can be managed.

Water vapor was introduced into gas mixtures by bubbling nitrogen gas through a water bath kept at constant temperature. The main impact of water vapor was to increase the background current of voltammograms as shown in FIGS. 16A-16D. The $NO_x$ signal, however, can still be determined among the background.

EXAMPLE V

Other Gases

The simultaneous effect of other gases on an $NO_x$ sensor was further studied by testing sensor performance in gas mixtures containing $CO_2$, $CH_4$, $O_2$, and $H_2O$. Two special cases were investigated in detail. Sensor response to changes in $NO_x$ concentration was studied when the concentrations of all other gases were kept constant. The sensor response is shown in FIGS. 17A-17D. Clearly, with the existence of 10% $CO_2$, 100 ppm $CH_4$, 0.4% $O_2$ and 3% $H_2O$, the sensor still responded to $NO_x$ very well from 500 ppm to 100 ppm. Sensor response to changes in oxygen concentration was studied when the concentrations of all other species were kept constant. The sensor response in shown in FIGS. 18A-18D. When the concentration of $NO_x$ was kept at 330 ppm in the gas mixtures, the oxygen signal can be easily determined when its concentration was higher than 0.2%. The current peak for $NO_x$ was still obvious even with the existence of 4.2% oxygen. The position of the $NO_x$ current peak also did not move when the oxygen concentration was changed from 0.2% to 4.2% in the gas mixtures. In both cases, no other peaks appeared in the voltage range studied other than the peaks due to the reduction of $NO_x$ and $O_2$, indicating that the sensor was inert to the other gases such as $CO_2$ and $CH_4$.

Although the invention has been described with a certain degree of particularity, this has been to illustrate the invention's principles, and should not be construed as limiting. Various changes and modifications can be made without departing from the scope of the appended claims.

What is claimed is:

1. A multi-functional sensor for sensing gaseous components in an exhaust stream from a combustion system comprising:

a solid electrolyte membrane comprised of an ion-conductive oxide material and having a thickness for selectively conducting ions from a gaseous component through said thickness, and further having a first surface proximal said exhaust stream, and a second surface opposite said first surface and isolated from said exhaust stream;

a plurality of sensing electrodes associated with the first surface of said solid electrolyte membrane and in fluid communication with said exhaust stream, each of said sensing electrodes comprised of a substrate of finely divided conductive particles underneath a catalyst capable of catalyzing a first oxidation or reduction reaction of a specific gaseous component in the exhaust stream, each of said sensing electrodes having high selectivity for electrochemical reduction or oxidation of a particular component of said exhaust stream;

a counter-electrode associated with said second surface of said solid electrolyte membrane, said counter-electrode comprised of finely divided particles of an electrode material capable of catalyzing a reduction or oxidation reaction of the specific gaseous component, opposite to that of the oxidation or reduction reaction occurring at the sensing electrodes;

a circuit electrically connecting said sensing electrodes and counter-electrode for enabling application of an electrical potential across said sensing electrodes and counter-electrode, and for enabling a current flux to flow between the sensing and counter-electrodes; and a meter for determining current flux between a sensing electrode and said counter-electrode.

2. A multi-functional sensor for sensing gaseous components in an exhaust stream from a combustion system comprising:

a solid electrolyte membrane comprised of an ion-conductive oxide material and having a thickness for selectively conducting ions from a gaseous component through said thickness, and further having a first surface proximal said exhaust stream, and a second surface opposite said first surface and isolated from said exhaust stream;

a plurality of sensing electrodes associated with the first surface of said solid electrolyte membrane and in fluid communication with said exhaust stream, each of said sensing electrodes comprised of a substrate of finely divided conductive particles underneath a catalyst capable of catalyzing a first oxidation or reduction reaction of a specific gaseous component in the exhaust stream, each of said sensing electrodes having high selectivity for electrochemical reduction or oxidation of a particular component of said exhaust stream;

a counter-electrode associated with said second surface of said solid electrolyte membrane, said counter-electrode comprised of finely divided particles of an electrode material capable of catalyzing a reduction or oxidation reaction of the specific gaseous component, opposite to that of the oxidation or reduction reaction occurring at a sensing electrode;

a reference electrode associated with the second surface and in fluid communication with a gas suitable for reference, said reference electrode comprised of a noble metal;

a circuit electrically connecting said sensing electrodes and the reference electrode for enabling an electrical potential across said sensing electrodes and reference electrode, and for enabling a current flux to flow between the sensing and counter-electrodes; and a meter for determining current flux between a sensing electrode and said counter-electrode.

3. The multi-functional sensor of claim 1 or claim 2 further comprising a diffusion barrier covering said sensing electrodes for limiting the amount of exhaust gas in fluid communication with said sensing electrodes, said diffusion barrier having a aperture therein in fluid communication with the exhaust stream.

4. The multi-functional sensor of claim 3 further comprising an exhaust gas compartment disposed between said diffusion barrier and said solid electrolyte membrane and in fluid communication with said aperture.

5. The multi-functional sensor of claim 3 wherein said diffusion barrier comprises alumina.

6. The multi-functional sensor of claim 2 wherein said reference electrode is of platinum.

7. A multi-functional sensor for sensing oxygen-containing gaseous components in an exhaust stream from a combustion system comprising:

a solid electrolyte membrane having a thickness and comprised of an ion-conductive oxide material selectively conducting oxygen ions through said thickness, and further having a first surface proximal said exhaust stream, and a second surface opposite said first surface and isolated from said exhaust stream;

a plurality of sensing electrodes associated with said first surface of said solid electrolyte membrane and in fluid communication with said exhaust stream, each of said sensing electrodes comprised of a substrate of finely divided conductive particles underneath a catalyst capable of catalyzing electrochemical reduction of an oxygen-containing gaseous component in the exhaust stream, each of said sensing electrodes having high selectivity for electrochemical reduction or oxidation of a particular component of said exhaust stream;

a counter-electrode associated with the second surface of said solid electrolyte membrane, said counter-electrode comprised of finely divided particles of an electrode material suitable for catalyzing electrochemical oxidation of oxygen ions conducted through said thickness of said solid electrolyte membrane;

a circuit electrically connecting said sensing electrodes and counter-electrode for enabling a current flux to flow between the sensing and counter-electrodes;

a meter for determining current flux between a sensing electrode and said counter-electrode;

a diffusion barrier covering said sensing electrodes for limiting the amount of exhaust gas in fluid communication with said sensing electrodes, said diffusion barrier having an aperture therein in fluid communication with the exhaust stream; and an exhaust gas compartment disposed between said diffusion barrier and said solid electrolyte membrane and in fluid communication with said diffusion aperture for receiving a portion of said exhaust gas in said exhaust stream through said diffusion aperture.

8. The multi-functional sensor of claim 7 wherein one of said sensing electrodes selectively electrochemically reduces a specific oxygen-containing component of said exhaust stream.

9. A multi-functional sensor for sensing hydrogen-containing gaseous components in an exhaust stream from a combustion control system comprising:

a solid electrolyte membrane having a thickness and comprised of an ion conductive oxide for selectively conducting protons through said thickness, and having a first surface proximal said exhaust stream, and a second surface opposite said first surface and isolated from said exhaust stream;

a sensing electrode associated with said first surface of said solid electrolyte membrane and in fluid communication with said exhaust stream, said sensing electrode comprised of finely divided particles of catalyst capable of catalyzing electrochemical oxidation of a hydrogen-containing gaseous component;

a counter-electrode associated with the second surface of said solid electrolyte membrane, said counter-electrode comprised of finely divided particles of an electrode material capable of catalyzing electrochemically reducing the protons conducted through the thickness of said solid electrolyte membrane;

a circuit electrically connecting said sensing electrode and counter-electrode for enabling a current flux to flow between the sensing and counter-electrodes;

a meter for determining the current flux between said sensing electrode and said counter-electrode;

a diffusion barrier covering said sensing electrode for limiting the amount of said exhaust gas in fluid communication with said sensing electrode, said diffusion barrier having an aperture extending therethrough in fluid communication with the exhaust stream; and an exhaust gas compartment disposed between said diffusion barrier and said solid electrolyte membrane and in fluid communication with said aperture for sampling a portion of the exhaust gas in the exhaust stream through the aperture.

10. The multi-functional sensor of claim 9 wherein said sensing electrode has high selectivity for electrochemically oxidizing a specific hydrogen-containing component of said exhaust stream.

11. The multi-functional sensor of claim 10 including a plurality of said sensing electrodes, each said sensing electrode having high selectivity for electrochemically oxidizing a specific hydrogen-containing component of said exhaust stream.

12. The multi-functional sensor of claim 9 or claim 13 wherein said diffusion barrier comprises alumina.

13. A multi-functional sensor for sensing hydrogen-containing gaseous components in an exhaust stream from a combustion control system comprising:

a solid electrolyte membrane having a thickness and comprised of an ion conductive oxide for selectively conducting protons through said thickness, and having a first surface proximal said exhaust stream, and a second surface opposite said first surface and isolated from said exhaust stream;

a sensing electrode associated with said first surface of said solid electrolyte membrane and in fluid communication with said exhaust stream, said sensing electrode comprised of finely divided particles of catalyst capable of catalyzing electrochemical oxidation of a hydrogen-containing gaseous component;

a counter-electrode associated with the second surface of said solid electrolyte membrane, said counter-electrode comprised of finely divided particles of an electrode material capable of catalyzing electrochemically reducing the protons conducted through the thickness of said solid electrolyte membrane;

a reference electrode associated with the second surface and in fluid communication with a gas suitable for reference, said reference electrode comprised of a noble metal; a circuit electrically connecting said sensing electrode and reference electrode for enabling an electrical potential across said sensing electrode and reference electrode, and for enabling a current flux to flow between the sensing and counter-electrodes;

a meter for determining the current flux between said sensing electrode and said counter-electrode;

a diffusion barrier covering said sensing electrode for limiting the amount of said exhaust gas in fluid communication with said sensing electrode, said diffusion barrier having an aperture extending therethrough in fluid communication with the exhaust stream; and an exhaust gas compartment disposed between said diffusion barrier and said solid electrolyte membrane and in fluid communication with said aperture for sampling a portion of the exhaust gas in the exhaust stream through the aperture.

14. The multi-functional sensor of claim 13 wherein said reference electrode is of platinum.

15. A multi-functional sensor for sensing oxygen-containing gaseous components in an exhaust stream from a combustion system comprising:

a solid electrolyte membrane having a thickness and comprised of an ion-conductive oxide material selectively conducting oxygen ions through said thickness, and further having a first surface proximal said exhaust stream, and a second surface opposite said first surface and isolated from said exhaust stream;

a plurality of sensing electrodes associated with said first surface of said solid electrolyte membrane and in fluid communication with said exhaust stream, each of said sensing electrodes comprised of a substrate of finely divided conductive particles underneath a catalyst capable of catalyzing electrochemical reduction of an oxygen-containing gaseous component in the exhaust stream, each of said sensing electrodes having high selectivity for electrochemical reduction or oxidation of a particular component of said exhaust stream;

a counter-electrode associated with the second surface of said solid electrolyte membrane, said counter-electrode comprised of finely divided particles of an electrode material suitable for catalyzing electrochemical oxidation of oxygen ions conducted through said thickness of said solid electrolyte membrane;

a reference electrode associated with the second surface and in fluid communication with a gas suitable for reference, said reference electrode comprised of a noble metal;

a circuit electrically connecting said sensing electrodes and reference electrode;

a meter for determining current flux between a sensing electrode and said counter-electrode;

a diffusion barrier covering said sensing electrode for limiting the amount of exhaust gas in fluid communication with said sensing electrodes, said diffusion barrier having an aperture therein in fluid communication with the exhaust stream; and an exhaust gas compartment disposed between said diffusion barrier and said solid electrolyte membrane and in fluid communication with said diffusion aperture for receiving a portion of said exhaust gas in said exhaust stream through said diffusion aperture.

* * * * *